(12) United States Patent
Osaka et al.

(10) Patent No.: US 9,051,274 B2
(45) Date of Patent: Jun. 9, 2015

(54) TRIARYLAMINE COMPOUND, LIGHT-EMITTING ELEMENT, LIGHT-EMITTING DEVICE, ELECTRONIC DEVICE, AND LIGHTING DEVICE

(75) Inventors: Harue Osaka, Kanagawa (JP); Takahiro Ushikubo, Tochigi (JP); Tsunenori Suzuki, Kanagawa (JP); Nobuharu Ohsawa, Tochigi (JP)

(73) Assignee: SEMICONDUCTOR ENERGY LABORATORY CO., LTD., Kanagawa-Ken (JP)

( * ) Notice: Subject to any disclaimer, the term of this patent is extended or adjusted under 35 U.S.C. 154(b) by 96 days.

(21) Appl. No.: 13/529,158

(22) Filed: Jun. 21, 2012

(65) Prior Publication Data
US 2012/0330025 A1 Dec. 27, 2012

(30) Foreign Application Priority Data
Jun. 24, 2011 (JP) .................. 2011-140508

(51) Int. Cl.
*C07D 263/54* (2006.01)
*C07D 235/04* (2006.01)
*C07D 235/18* (2006.01)
*C07D 263/57* (2006.01)
*H01L 51/00* (2006.01)

(52) U.S. Cl.
CPC ............ *C07D 235/18* (2013.01); *C07D 263/57* (2013.01); *H01L 51/0061* (2013.01); *H01L 51/0071* (2013.01)

(58) Field of Classification Search
CPC ............................ C07D 263/54; C07D 235/04
USPC ................................................ 548/219, 309.7
See application file for complete search history.

(56) References Cited

U.S. PATENT DOCUMENTS

| | | | |
|---|---|---|---|
| 8,329,917 B2 * | 12/2012 | Nomura et al. ............... | 548/224 |
| 2008/0099757 A1 | 5/2008 | Furukawa et al. | |
| 2008/0254318 A1 | 10/2008 | Nakashima et al. | |
| 2008/0284328 A1 | 11/2008 | Nakashima et al. | |
| 2009/0015140 A1 | 1/2009 | Kawakami et al. | |
| 2009/0058267 A1 | 3/2009 | Nakashima et al. | |
| 2010/0069647 A1 | 3/2010 | Suzuki et al. | |

FOREIGN PATENT DOCUMENTS

| | | | | |
|---|---|---|---|---|
| JP | 3045799 | * | 3/2000 | .................... 548/200 |
| JP | 2003-267972 | | 9/2003 | |

* cited by examiner

*Primary Examiner* — Samantha Shterengarts
(74) *Attorney, Agent, or Firm* — Husch Blackwell LLP

(57) ABSTRACT

A novel triarylamine compound having a bipolar property is provided. The triarylamine compound can be used for a hole-injection layer, a hole-transport layer, a light-emitting layer, or an electron-transport layer in a light-emitting element. The triarylamine compound can also be used as a host material with a light-emitting material which emits relatively short-wavelength light, in a structure where the host material and the guest material constitute a light-emitting layer. The triarylamine compound of the present invention is a fluorescent compound and therefore can also be used as a light-emitting substance of a light-emitting layer. A light-emitting element having high emission efficiency is provided. A light-emitting device, an electronic device, or a lighting device having low power consumption is provided.

25 Claims, 23 Drawing Sheets

FIG. 6A
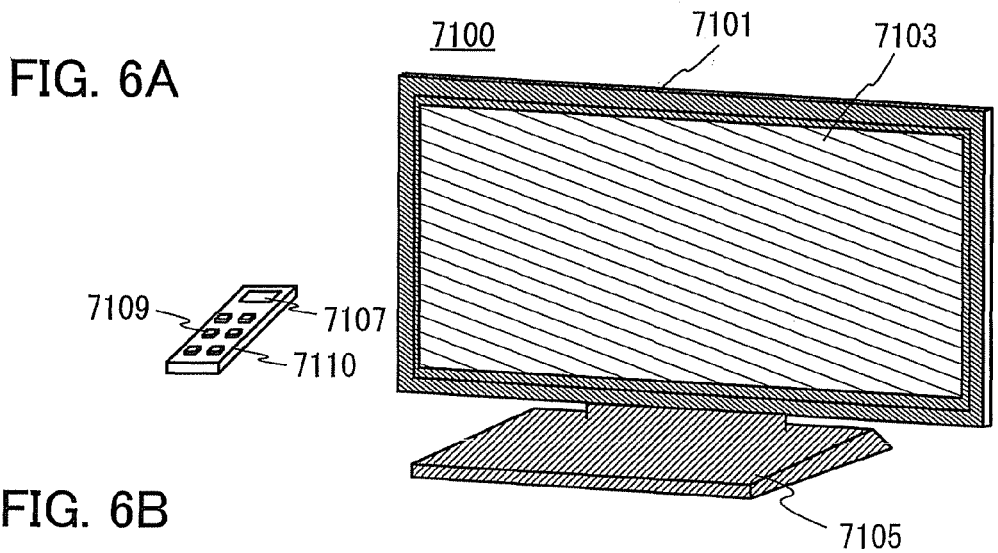
FIG. 6B
FIG. 6C
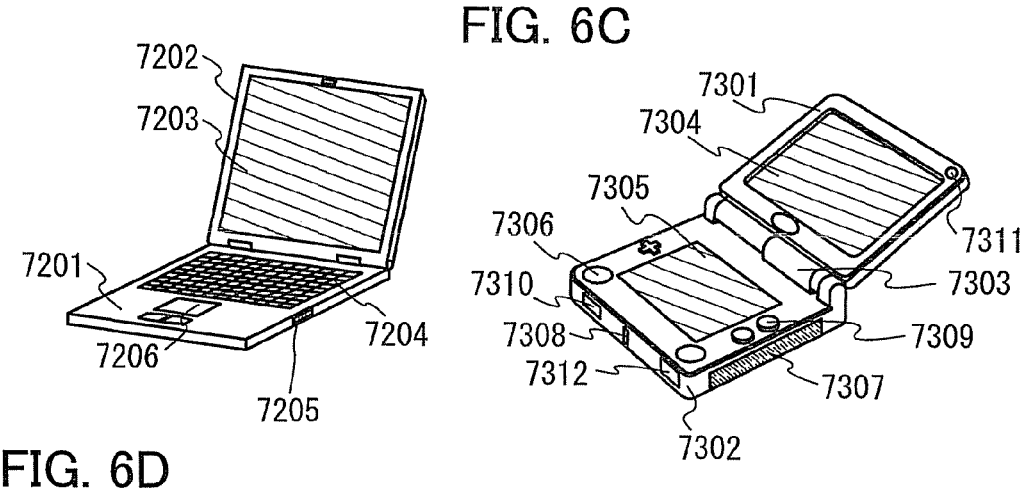
FIG. 6D
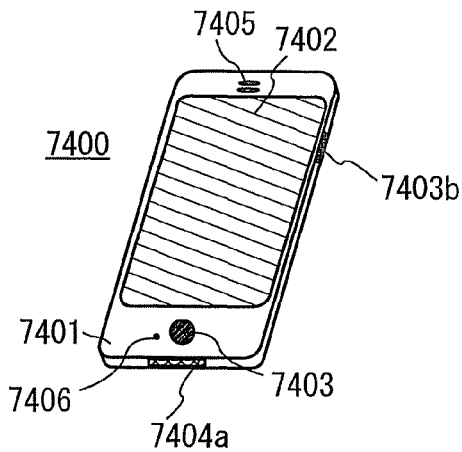

(a) Toluene solution of BPABIm (b) Thin film of BPABIm (a) Toluene solution of BOxABP (b) Thin film of BOxABP

TRIARYLAMINE COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a triarylamine compound. In addition, one embodiment of the present invention relates to a light-emitting element, a light-emitting device, an electronic device, and a lighting device each of which uses the triarylamine compound.

2. Description of the Related Art

In recent years, research and development of light-emitting elements using electroluminescence (EL) have been actively conducted. In a basic structure of such a light-emitting element, a layer containing a light-emitting substance is interposed between a pair of electrodes. By voltage application to this element, light emission can be obtained from the light-emitting substance.

Such a light-emitting element is of self-luminous type, and thus has advantages over a liquid crystal display in that visibility of pixels is high, backlight is not needed, and so on. Therefore, such a light-emitting element is regarded as being suitable as a flat panel display element. Besides, such a light-emitting element has advantages in that it can be manufactured to be thin and lightweight, and has very fast response speed.

Furthermore, since such light-emitting elements can be formed in a film form, they make it possible to provide planar light emission easily; thus, large-area elements using planar light emission can be formed. This is a feature that is difficult to obtain with point light sources typified by an incandescent lamp and an LED or linear light sources typified by a fluorescent lamp. Therefore, the light-emitting element is very effective for use as a surface light source applicable to a lighting device and the like.

Light-emitting elements utilizing electroluminescence are broadly classified according to whether they use an organic compound or an inorganic compound as a light-emitting substance. In the case where an organic compound is used as a light-emitting substance, by application of voltage to a light-emitting element, electrons and holes are injected into a layer containing the light-emitting organic compound from a pair of electrodes, whereby current flows. Then, with these carriers (i.e., electrons and holes), the light-emitting organic compound is brought into an excited state. The light-emitting organic compound returns to the ground state from the excited state, thereby emitting light.

Because of such a mechanism, the light-emitting element is called a current-excitation light-emitting element. Note that the excited state of an organic compound can be a singlet excited state and a triplet excited state, and luminescence from the singlet excited state is referred to as fluorescence, and luminescence from the triplet excited state is referred to as phosphorescence.

In improving element characteristics of such light-emitting elements, there are a lot of problems that depend on substances, and in order to solve the problems, improvement of the element structures, development of the substances, and the like have been carried out (e.g., Patent Document 1)

REFERENCE

Patent Document

[Patent Document 1] Japanese Published Patent Application No. 2003-267972

SUMMARY OF THE INVENTION

In accordance with one embodiment of the present invention, a novel triarylamine compound which has both a hole-transport property and an electron-transport property, i.e., a so-called bipolar property, is provided. In accordance with one embodiment of the present invention, a light-emitting element with high emission efficiency is provided. In accordance with one embodiment of the present invention, a light-emitting device, an electronic device, or a lighting device with low power consumption are provided.

One embodiment of the present invention is a triarylamine compound. Thus, one embodiment of the present invention is a triarylamine compound represented by a general formula (G1) below.

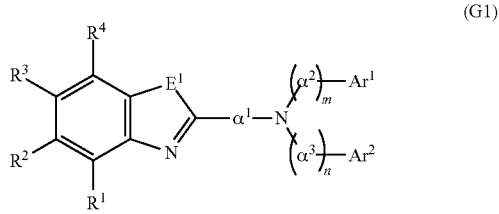

(G1)

Note that in the formula, $E^1$ represents an oxygen atom or a nitrogen atom, and when $E^1$ represents a nitrogen atom, a substituted or unsubstituted phenyl group or a substituted or unsubstituted biphenyl group is bonded to the nitrogen atom. Further, $\alpha^1$ to $\alpha^3$ each independently represent a substituted or unsubstituted phenylene group or a substituted or unsubstituted biphenylene group, and m and n are each independently 0 or 1. In addition, $Ar^1$ represents any of a substituted or unsubstituted phenyl group, a substituted or unsubstituted naphthyl group, a substituted or unsubstituted triphenylenyl group, a substituted or unsubstituted fluorenyl group, a substituted or unsubstituted carbazolyl group, a substituted or unsubstituted dibenzothiophenyl group, a substituted or unsubstituted dibenzofuranyl group, and an aryl group represented by a general formula (G1-2) given below. Further, $Ar^2$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^1$ to $R^4$ each independently represent any of a hydrogen atom, an alkyl group having 1 to 6 carbon atoms, and a substituted or unsubstituted phenyl group.

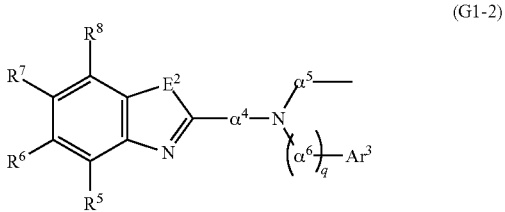

(G1-2)

Note that in the formula, $E^2$ represents an oxygen atom or a nitrogen atom, and when $E^2$ represents a nitrogen atom, a substituted or unsubstituted phenyl group or a substituted or unsubstituted biphenyl group is bonded to the nitrogen atom. In addition, $\alpha^4$ to $\alpha^6$ each independently represent a substituted or unsubstituted phenylene group or a substituted or unsubstituted biphenylene group, and q is 0 or 1. Further, $Ar^3$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^5$ to $R^8$ each independently represent any of a hydrogen atom, an alkyl group having 1 to 6 carbon atoms, and a substituted or unsubstituted phenyl group.

Another embodiment of the present invention is a triarylamine compound represented by a general formula (G2) below.

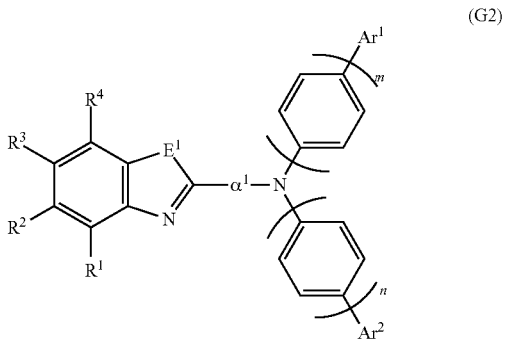

(G2)

Note that in the formula, $E^1$ represents an oxygen atom or a nitrogen atom, and when $E^1$ represents a nitrogen atom, a substituted or unsubstituted phenyl group or a substituted or unsubstituted biphenyl group is bonded to the nitrogen atom. Further, $\alpha^1$ represents a substituted or unsubstituted phenylene group or a substituted or unsubstituted biphenylene group, and m and n are each independently 0 or 1. In addition, $Ar^1$ represents any of a substituted or unsubstituted phenyl group, a substituted or unsubstituted naphthyl group, a substituted or unsubstituted triphenylenyl group, a substituted or unsubstituted fluorenyl group, a substituted or unsubstituted carbazolyl group, a substituted or unsubstituted dibenzothiophenyl group, a substituted or unsubstituted dibenzofuranyl group, and an aryl group represented by a general formula (G2-2) given below. Further, $Ar^2$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^1$ to $R^4$ each independently represent any of a hydrogen atom, an alkyl group having 1 to 6 carbon atoms, and a substituted or unsubstituted phenyl group.

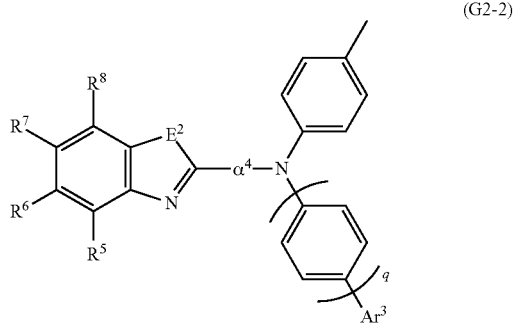

(G2-2)

Note that in the formula, $E^2$ represents an oxygen atom or a nitrogen atom, and when $E^2$ represents a nitrogen atom, a substituted or unsubstituted phenyl group or a substituted or unsubstituted biphenyl group is bonded to the nitrogen atom. In addition, $\alpha^4$ represents a substituted or unsubstituted phenylene group or a substituted or unsubstituted biphenylene group, and q is 0 or 1. Further, $Ar^3$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^5$ to $R^8$ each independently represent any of a hydrogen atom, an alkyl group having 1 to 6 carbon atoms, and a substituted or unsubstituted phenyl group.

A further embodiment of the present invention is a triarylamine compound represented by a general formula (G3) below.

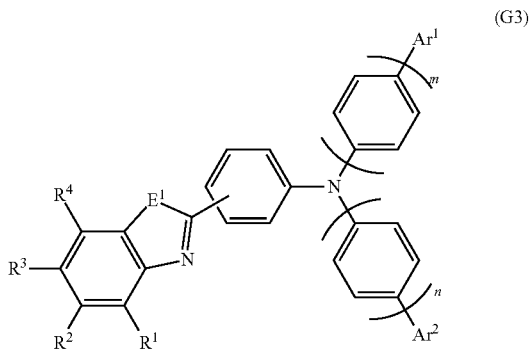

(G3)

Note that in the formula, $E^1$ represents an oxygen atom or a nitrogen atom, and when $E^1$ represents a nitrogen atom, a substituted or unsubstituted phenyl group or a substituted or unsubstituted biphenyl group is bonded to the nitrogen atom. Further, m and n are each independently 0 or 1. In addition, $Ar^1$ represents any of a substituted or unsubstituted phenyl group, a substituted or unsubstituted naphthyl group, a substituted or unsubstituted triphenylenyl group, a substituted or unsubstituted fluorenyl group, a substituted or unsubstituted carbazolyl group, a substituted or unsubstituted dibenzothiophenyl group, a substituted or unsubstituted dibenzofuranyl group, and an aryl group represented by a general formula (G3-2) given below. Further, $Ar^2$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^1$ to $R^4$ each independently represent any of a hydrogen atom, an alkyl group having 1 to 6 carbon atoms, and a substituted or unsubstituted phenyl group.

(G3-2)

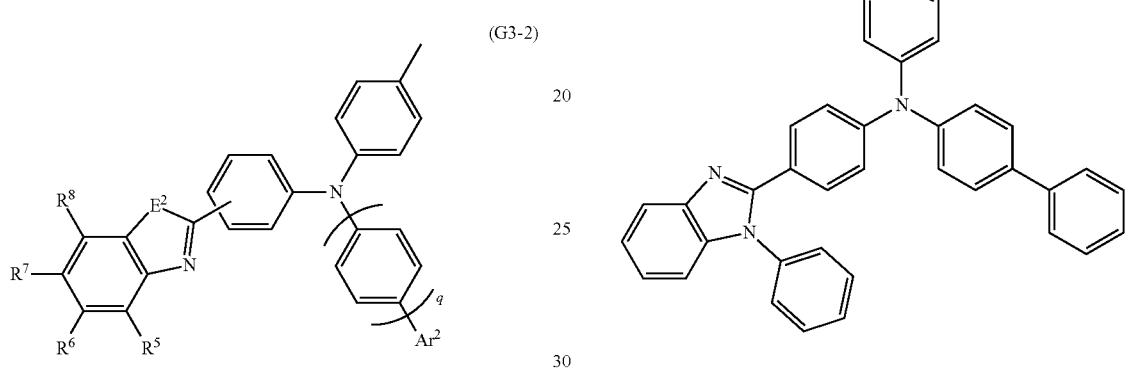

Note that in the formula, $E^2$ represents an oxygen atom or a nitrogen atom, and when $E^2$ represents a nitrogen atom, a substituted or unsubstituted phenyl group or a substituted or unsubstituted biphenyl group is bonded to the nitrogen atom. In addition, q is 0 or 1. Further, $Ar^3$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^5$ to $R^8$ each independently represent any of a hydrogen atom, an alkyl group having 1 to 6 carbon atoms, and a substituted or unsubstituted phenyl group.

A yet still further embodiment of the present invention is a triarylamine compound represented by a structural formula (100) below.

(100)

A yet still further embodiment of the present invention is a triarylamine compound represented by a structural formula (135) below.

(135)

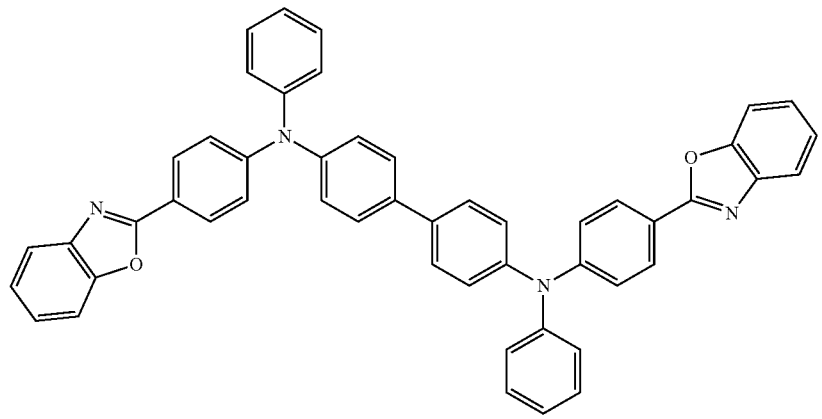

A triarylamine compound of the present invention has both a hole-transport property and an electron-transport property, i.e., is a so-called bipolar property. In addition, the triarylamine compound features good thermophysical properties and a high level of amorphousness. Therefore, the triarylamine compound can be used for a hole-injection layer, a hole-transport layer, a light-emitting layer, or an electron-transport layer in a light-emitting element. Further, a triarylamine compound of the present invention has a structure in which amine is formed with a structure including a phenyl group bonded to a five-membered ring; thus, conjugation can be prevented from extending to another heterocyclic ring bonded to the amine. Hence, the triarylamine compound can also be used as a host material with a light-emitting material which emits relatively short-wavelength light, in a structure where the host material and the guest material (light-emitting material) constitute a light-emitting layer. Furthermore, a triarylamine compound of the present invention is a fluorescent compound and therefore can also be used as a light-emitting substance of a light-emitting layer. Thus, the present invention also includes a light-emitting element including a triarylamine compound of one embodiment of the present invention.

That is, a yet still further embodiment of the present invention is a light-emitting element which includes an EL layer between a pair of electrodes, where at least one of a light-emitting layer and a hole-transport layer which are included in the EL layer contains a triarylamine compound of one embodiment of the present invention.

Further, the present invention includes electronic devices and lighting devices including light-emitting devices as well as light-emitting devices including light-emitting elements. The light-emitting device in this specification refers to an image display device, a light-emitting device, and a light source (e.g., a lighting device). In addition, the light-emitting device includes, in its category, all of a module in which a light-emitting device is connected to a connector such as a flexible printed circuit (FPC), a tape automated bonding (TAB) tape or a tape carrier package (TCP), a module in which a printed wiring board is provided on the tip of a TAB tape or a TCP, and a module in which an integrated circuit (IC) is directly mounted on a light-emitting element by a chip on glass (COG) method.

Since a triarylamine compound of one embodiment of the present invention has a bipolar property, it can be used for a hole-injection layer, a hole-transport layer, a light-emitting layer, or an electron-transport layer which is included in an EL layer of a light-emitting element. Further, a light-emitting element, in which a triarylamine compound of one embodiment of the present invention is used for a hole-injection layer, a hole-transport layer, a light-emitting layer, an electron-transport layer, or the like, can have high emission efficiency. By the use of such a light-emitting element, a light-emitting device, an electronic device, and a lighting device each having low power consumption and low drive voltage can be provided.

BRIEF DESCRIPTION OF THE DRAWINGS

In the accompanying drawings:

FIGS. 6A to 6D illustrate electronic devices;

DETAILED DESCRIPTION OF THE INVENTION

Figure 1:
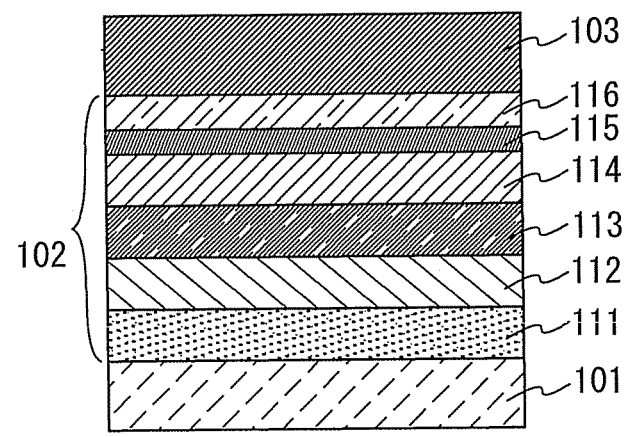
FIG. 1 illustrates a structure of a light-emitting element.

Hereinafter, embodiments of the present invention will be described in detail with reference to the accompanying drawings. Note that the present invention is not limited to the description below, and modes and details thereof can be modified in various ways without departing from the spirit and the scope of the present invention. Therefore, the present invention should not be construed as being limited to the description of the following embodiments.

Embodiment 1

In this embodiment, a triarylamine compound of one embodiment of the present invention is described.

A triarylamine compound of one embodiment of the present invention is represented by the following general formula (G1).

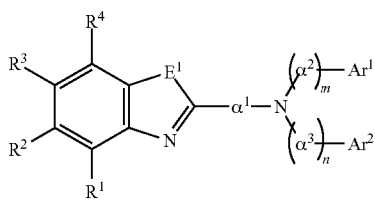
(G1)

In the general formula (G1), $E^1$ represents an oxygen atom or a nitrogen atom, and when $E^1$ represents a nitrogen atom, a substituted or unsubstituted phenyl group or a substituted or unsubstituted biphenyl group is bonded to the nitrogen atom. Further, $\alpha^1$ to $\alpha^3$ each independently represent a substituted or unsubstituted phenylene group or a substituted or unsubstituted biphenylene group, and m and n are each independently 0 or 1. In addition, $Ar^1$ represents any of a substituted or unsubstituted phenyl group, a substituted or unsubstituted naphthyl group, a substituted or unsubstituted triphenylenyl group, a substituted or unsubstituted fluorenyl group, a substituted or unsubstituted carbazolyl group, a substituted or unsubstituted dibenzothiophenyl group, a substituted or unsubstituted dibenzofuranyl group, and an aryl group represented by the general formula (G1-2) below. In addition, $Ar^2$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^1$ to $R^4$ each independently represent any of a hydrogen atom, an alkyl group having 1 to 6 carbon atoms, and a substituted or unsubstituted phenyl group.

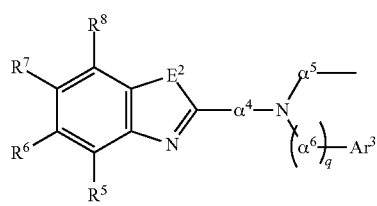
(G1-2)

Further, in the general formula (G1-2), $E^2$ represents an oxygen atom or a nitrogen atom, and when $E^2$ represents a nitrogen atom, a substituted or unsubstituted phenyl group, a substituted or unsubstituted biphenyl group is bonded to the nitrogen atom. In addition, $\alpha^4$ to $\alpha^6$ each independently represent a substituted or unsubstituted phenylene group or a substituted or unsubstituted biphenylene group, and q is 0 or 1. In addition, $Ar^3$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^5$ to $R^8$ each independently represent any of a hydrogen atom, an alkyl group having 1 to 6 carbon atoms, and a substituted or unsubstituted phenyl group.

The molecular weight of the triarylamine compound represented by the general formula (G1) is preferably greater than or equal to 430 in terms of heat resistance of the organic EL element. In the case where the triarylamine compound is Minted into a film by evaporation, the molecular weight is preferably less than or equal to 1000 in terms of sublimability. More preferably, the molecular weight is greater than or equal to 500 and less than or equal to 800.

Therefore, in the triarylamine compound represented by the general formula (G1), in the case where $E^1$ is a nitrogen atom, it is preferable in terms of molecular weight that $Ar^1$ represent any of a substituted or unsubstituted phenyl group, a substituted or unsubstituted naphthyl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group.

Here, specific examples of the phenylene or biphenylene group which is represented by $\alpha^1$ to $\alpha^6$ in the general formulae (G1) and (G1-2) are represented by structural formulae (s-1) to (s-8) below.

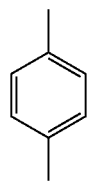
(s-1)

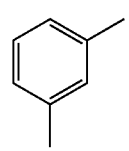
(s-2)

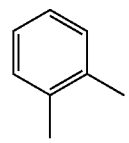
(s-3)

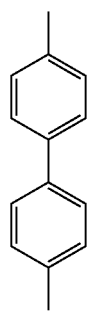
(s-4)

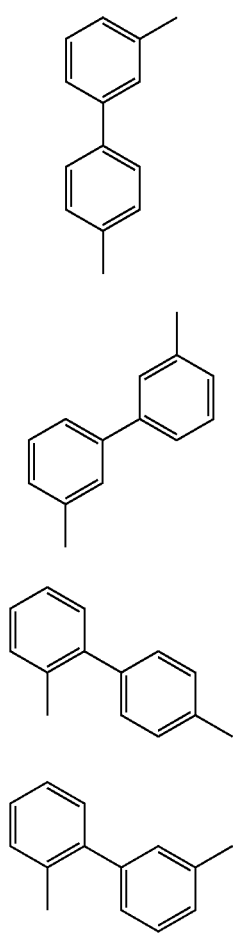

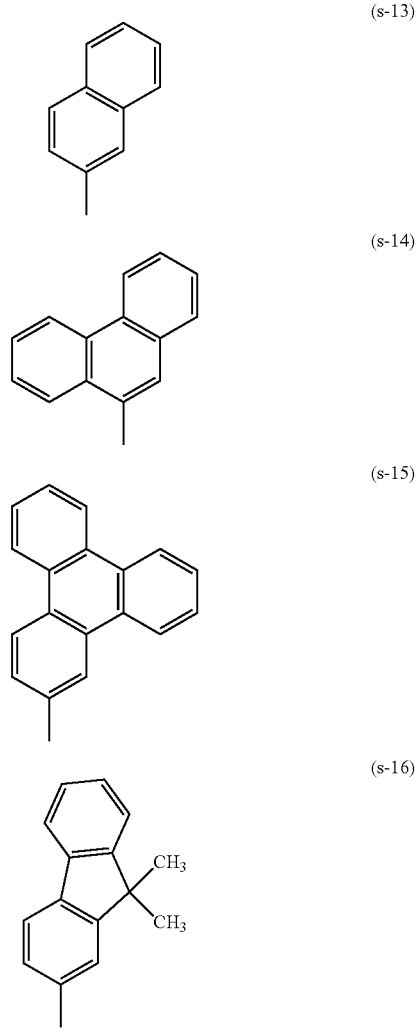

The bond at the meta-position or the ortho-position as in the formulae (s-2), (s-3), and (s-5) to (s-8) is preferred in that conjugation is unlikely to extend. The bond at the para-position as in the formulae (s-1) and (s-4) is preferred in that improved carrier-transport property and increased reliability can be expected.

Specific examples of Ar$^1$ to Ar$^3$ in the general formula (G1) are represented by the following structural formulae (s-11) to (s-25).

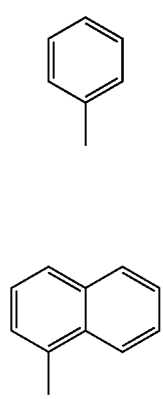

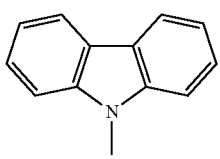
(s-19)

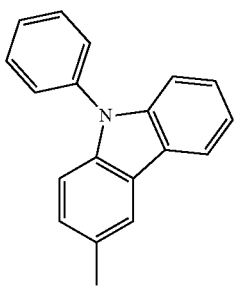
(s-20)

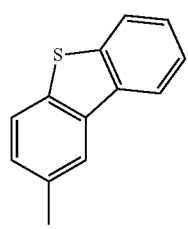
(s-21)

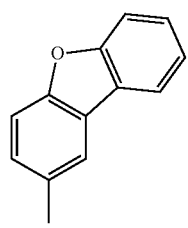
(s-22)

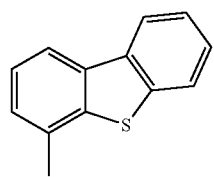
(s-23)

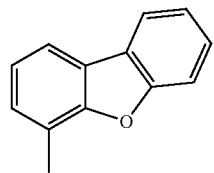
(s-24)

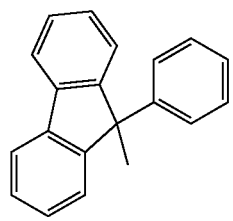
(s-25)

Substituents represented by the formulae (s-11) to (s-25) are preferred in that they are unlikely to allow extension of the conjugation and have a wide band gap. Aryl groups having a ring consisted of two or more rings, as illustrated in the formulae (s-12) to (s-25), are preferred in that they have a good carrier-transport property. A carbazolyl group, the 9-position or 3-position of which is substituted, and a dibenzothiophenyl or dibenzofuranyl group, the 2-position of which is substituted, as illustrated in the formulae (s-19) to (s-22), are preferred in that they have a good hole-transport property.

A triarylamine compound of one embodiment of the present invention is represented by the following general formula (G2).

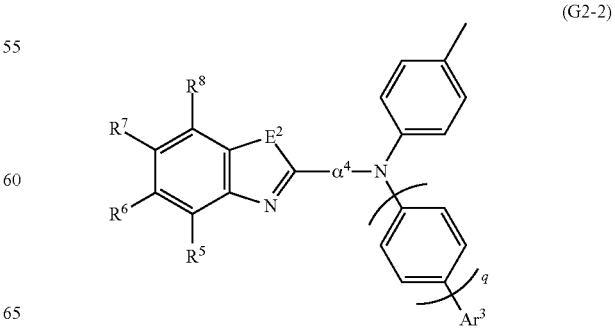

(G2)

In the general formula (G2), $E^1$ represents an oxygen atom or a nitrogen atom, and when $E^1$ represents a nitrogen atom, a substituted or unsubstituted phenyl group or a substituted or unsubstituted biphenyl group is bonded to the nitrogen atom. Further, $\alpha^1$ represents a substituted or unsubstituted phenylene group or a substituted or unsubstituted biphenylene group, and m and n are each independently 0 or 1. In addition, $Ar^1$ represents any of a substituted or unsubstituted phenyl group, a substituted or unsubstituted naphthyl group, a substituted or unsubstituted triphenylenyl group, a substituted or unsubstituted fluorenyl group, a substituted or unsubstituted carbazolyl group, a substituted or unsubstituted dibenzothiophenyl group, a substituted or unsubstituted dibenzofuranyl group, and an aryl group represented by a general formula (G2-2) given below. Further, $Ar^2$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^1$ to $R^4$ each independently represent any of a hydrogen atom, an alkyl group having 1 to 6 carbon atoms, and a substituted or unsubstituted phenyl group.

(G2-2)

Further, in the general formula (G2-2), $E^2$ represents an oxygen atom or a nitrogen atom, and when $E^2$ represents a nitrogen atom, a substituted or unsubstituted phenyl group or a substituted or unsubstituted biphenyl group is bonded to the nitrogen atom. Further, $\alpha^4$ represents a substituted or unsubstituted phenylene group or a substituted or unsubstituted biphenylene group, and q is 0 or 1. In addition, $Ar^3$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^5$ to $R^8$ each independently represent any of a hydrogen atom, an alkyl group having 1 to 6 carbon atoms, and a substituted or unsubstituted phenyl group.

Here, specific examples of $\alpha^1$, $\alpha^4$, $Ar^1$ $Ar^2$, and $Ar^3$ in the general formula (G2) or the general formula (G2-2) are $\alpha^1$, $\alpha^4$, $Ar^1$ $Ar^2$, and $Ar^3$ in the general formula (G1).

A triarylamine compound of one embodiment of the present invention is represented by the following general formula (G3).

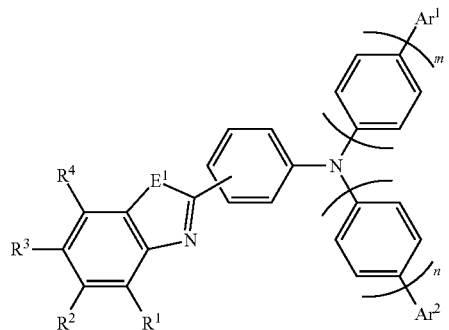

(G3)

In the general formula (G3), $E^1$ represents an oxygen atom or a nitrogen atom, and when $E^1$ represents a nitrogen atom, a substituted or unsubstituted phenyl group or a substituted or unsubstituted biphenyl group is bonded to the nitrogen atom. Further, m and n are each independently 0 or 1. In addition, $Ar^1$ represents any of a substituted or unsubstituted phenyl group, a substituted or unsubstituted naphthyl group, a substituted or unsubstituted triphenylenyl group, a substituted or unsubstituted fluorenyl group, a substituted or unsubstituted carbazolyl group, a substituted or unsubstituted dibenzothiophenyl group, a substituted or unsubstituted dibenzofuranyl group, and an aryl group represented by a general formula (G3-2) given below. Further, $Ar^2$ represents any of a substituted or unsubstituted phenyl group or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^1$ to $R^4$ each independently represent any of a hydrogen atom, an alkyl group having 1 to 6 carbon atoms, and a substituted or unsubstituted phenyl group.

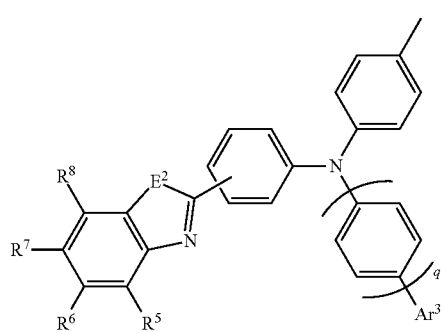

(G3-2)

Further, in the general formula (G3-2), $E^2$ represents an oxygen atom or a nitrogen atom, and when $E^2$ represents a nitrogen atom, a substituted or unsubstituted phenyl group or a substituted or unsubstituted biphenyl group is bonded to the nitrogen atom. In addition, q is 0 or 1. Further, $Ar^3$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group. Further, $R^5$ to $R^8$ each independently represent any of a hydrogen atom, an alkyl group having 1 to 6 carbon atoms, and a substituted or unsubstituted phenyl group.

Here, specific examples of $Ar^1$ $Ar^2$, and $Ar^3$ in the general formula (G3) or the general formula (G3-2) are $Ar^1$ $Ar^2$, and $Ar^3$ in the general formula (G1).

Note that the triarylamine compounds represented by the above general formulae (G1) to (G3) each preferably have a substituent so as to have an improved thermophysical property (Tg). Specific examples of the substituent are an alkyl group having 1 to 6 carbon atoms such as a methyl group, an ethyl group, or a tert-butyl group, a phenyl group, and the like.

Next, specific structural formulae of a triarylamine compound of one embodiment of the present invention are shown (the following structural formulae (100) to (118) and (130) to (136)). Note that the present invention is not limited thereto.

(100)
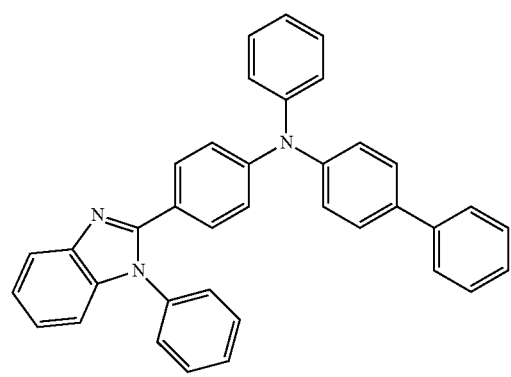
(101)
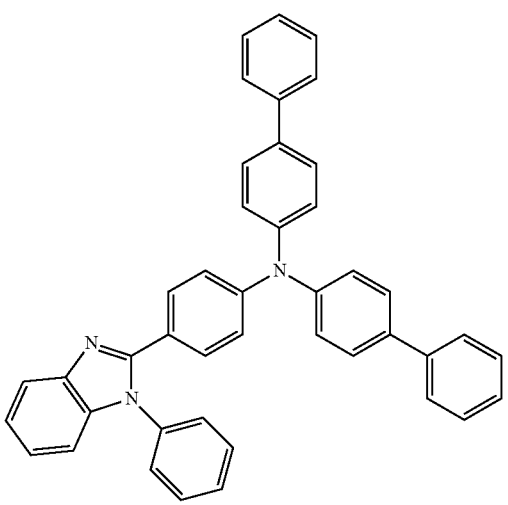
(102)
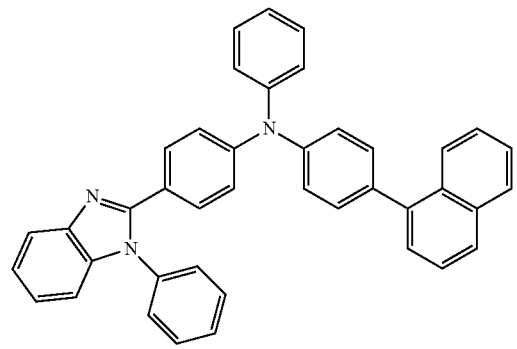
(103)
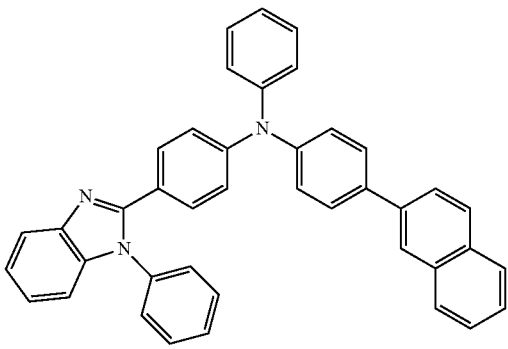
(104)
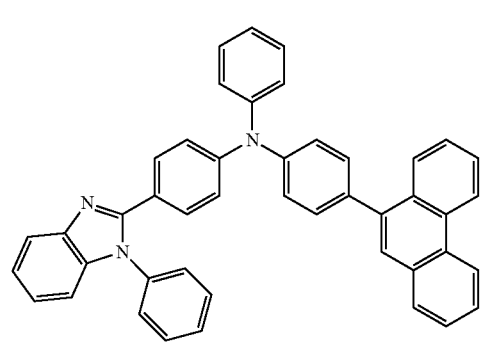
(105)
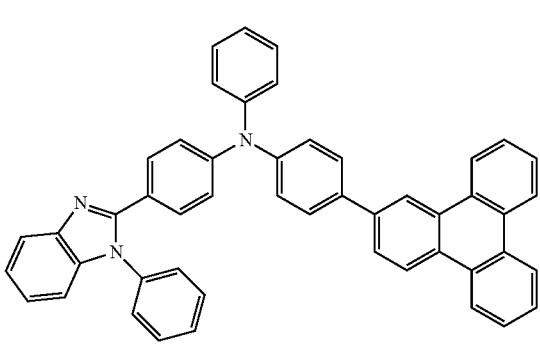
(106)
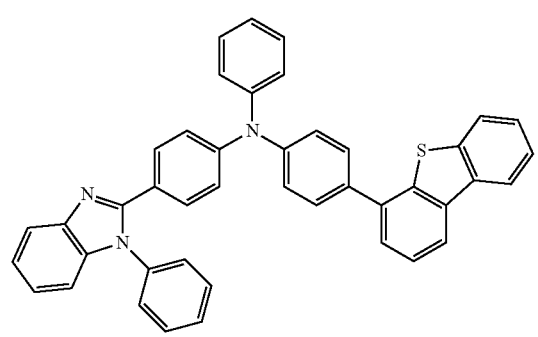
(107)
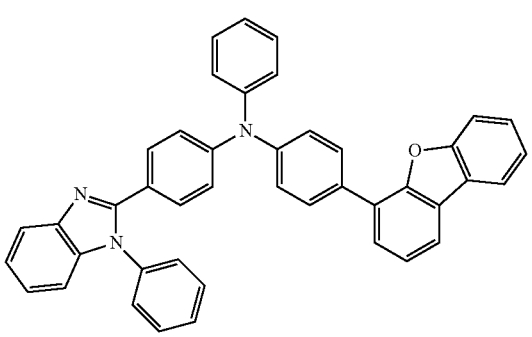

-continued
(108)
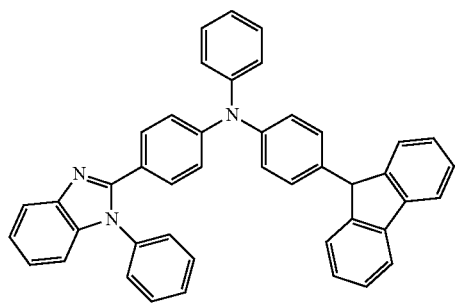
(109)
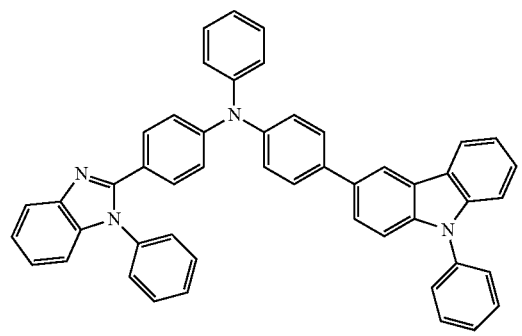
(110)
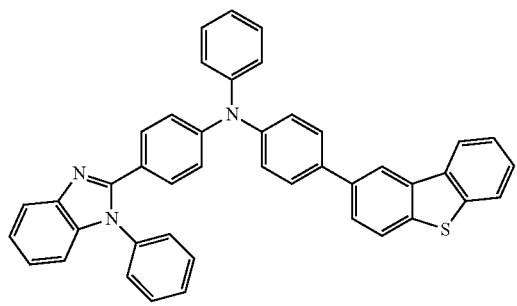
(111)
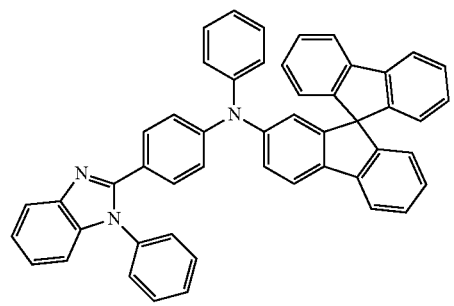
(112)
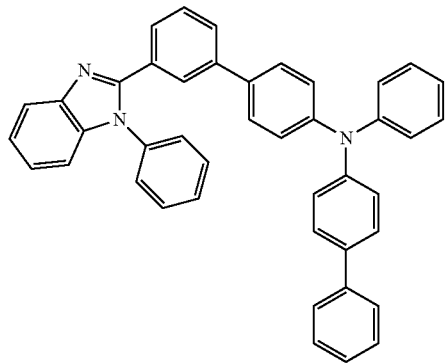
(113)
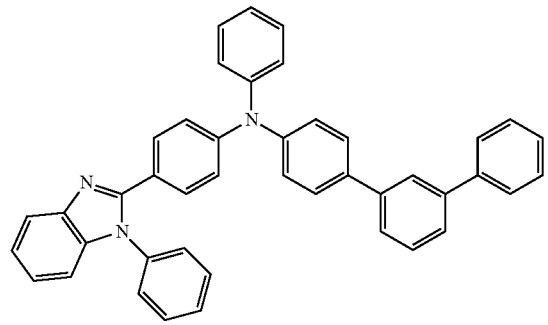
(114)
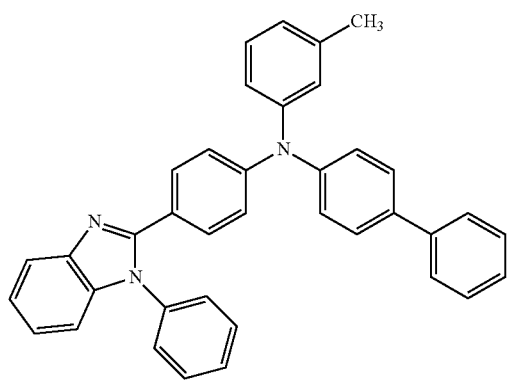
(115)
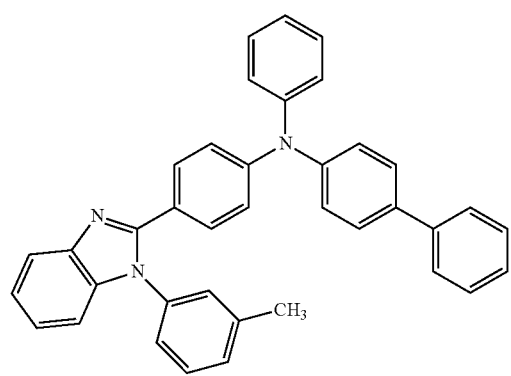

(116)
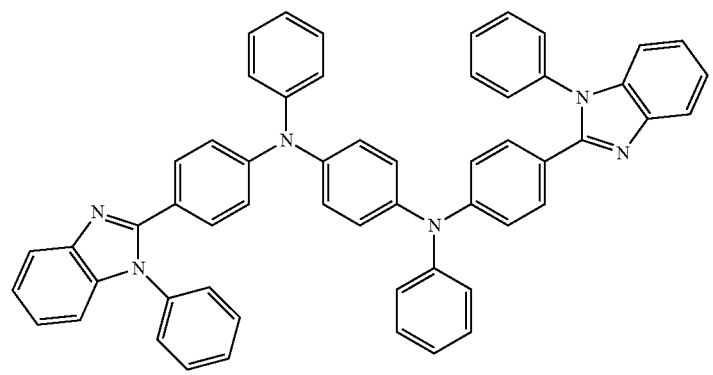
(117)
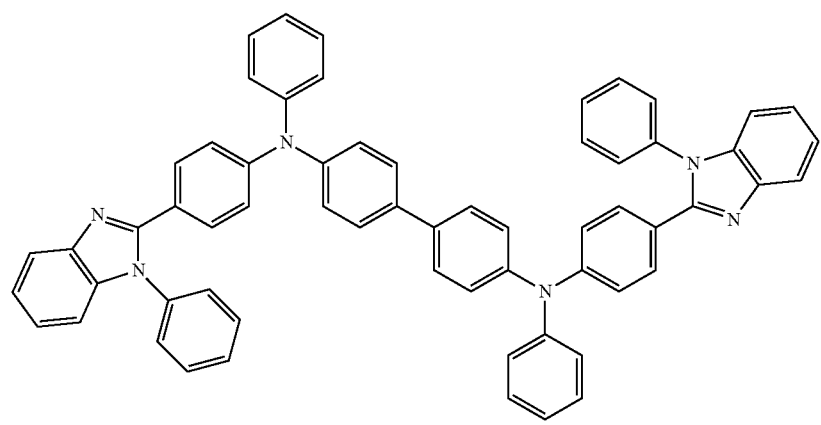
(118)
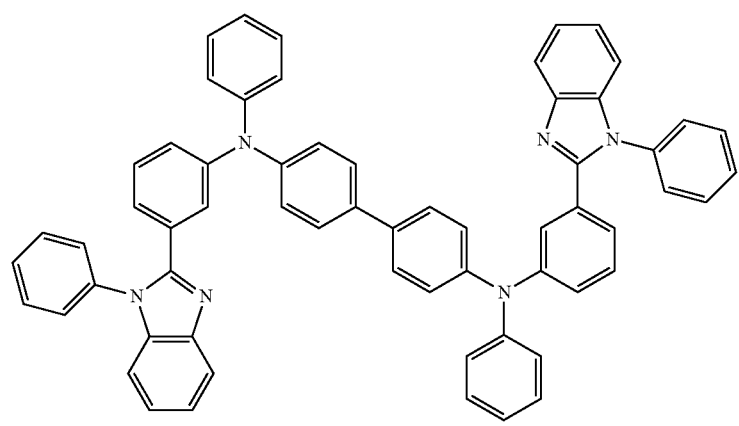

-continued
(130)
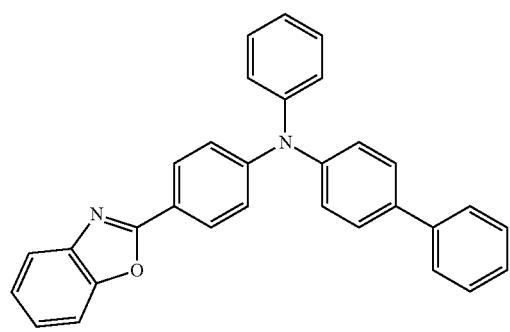
(131)
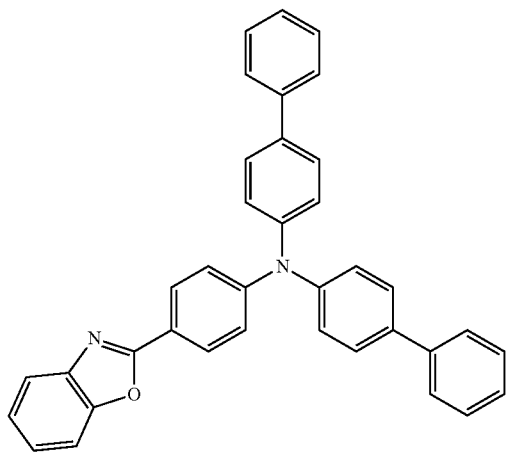
(132)
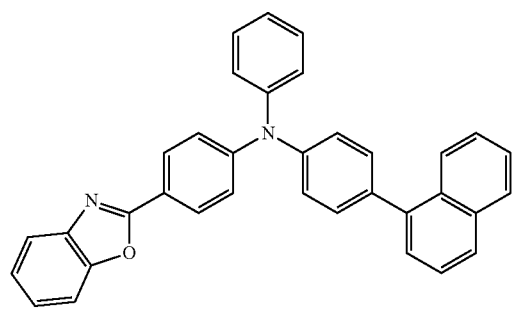
(133)
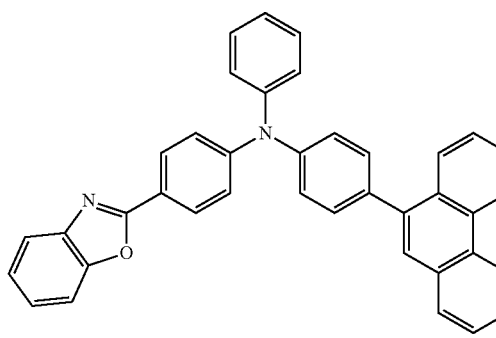
(134)
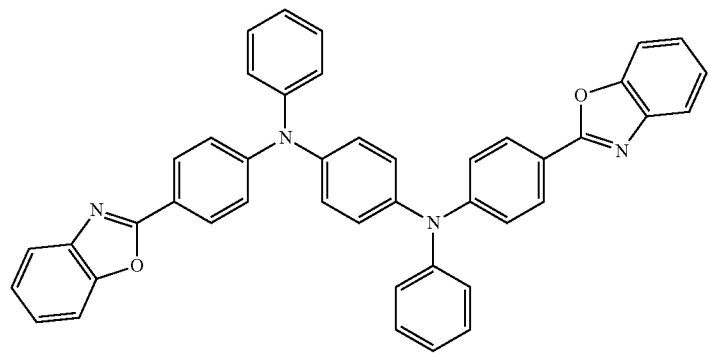
(135)
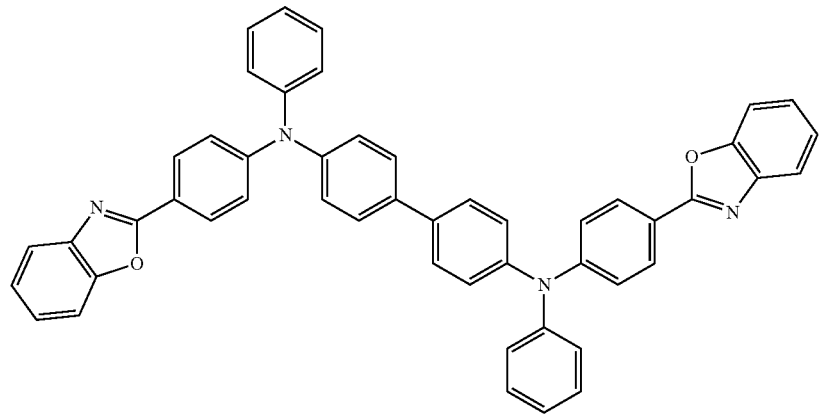

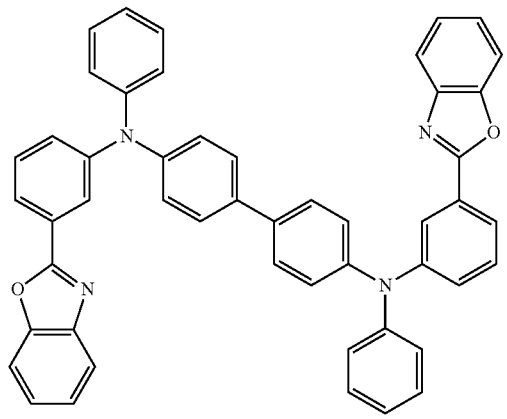

Note that the triarylamine compounds represented by the above structural formulae (100) to (118) and (130) to (136) are novel substances which have a bipolar property. Specifically, in each compound, the benzimidazolyl group or the benzoxazolyl group is a skeleton having an excellent electron-transport property and the triarylamine skeleton is a skeleton having an excellent hole-transport property.

Next, as an example of a method of synthesizing a triarylamine compound of one embodiment of the present invention, a method of synthesizing the triarylamine compound represented by the general formula (G1) is described.

Method of Synthesizing Triarylamine Compound Represented by General Formula (G1)

An example of a method of synthesizing the triarylamine compound represented by the general formula (G1) is described.

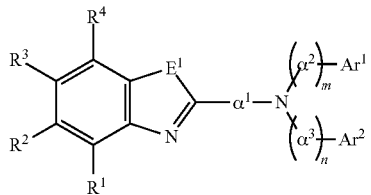

The triarylamine compound represented by the general formula (G1) can be synthesized by a synthesis method illustrated in a synthesis scheme (A) illustrated below.

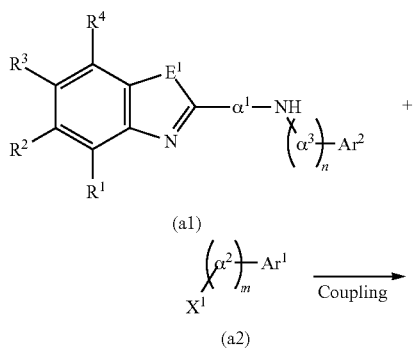

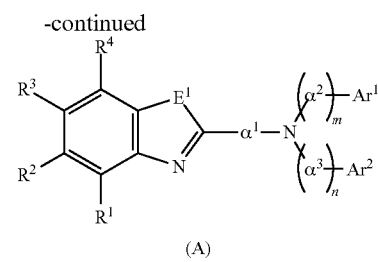

In the formula, $X^1$ represents halogen. As the halogen, iodine, bromine, and chlorine can facilitate the reaction and are preferred in this order.

As illustrated in the scheme (A), a diarylamine compound (a1) and a halogenated aryl compound (a2) undergo coupling, thereby forming the triarylamine compound represented by the above general formula (G1).

Note that there are a variety of reaction conditions for the reaction in the scheme (A). As an example, a synthesis method using a metal catalyst in the presence of a base can be employed.

The case where a Hartwig-Buchwald reaction is used in the above synthesis reaction is described. A palladium catalyst can be used as a metal catalyst, and a mixture of a palladium complex and a ligand thereof can be used as the palladium catalyst. Examples of the palladium catalyst are bis(dibenzylideneacetone)palladium(0), palladium(II) acetate, and the like. Examples of the ligand are tri(tert-butyl)phosphine, tri(n-hexyl)phosphine, tricyclohexylphosphine, 1,1-bis(diphenylphosphino)ferrocene (abbreviation: DPPF), and the like. Examples of a substance which can be used as a base are organic bases such as sodium-tert-butoxide, inorganic bases such as potassium carbonate, and the like. The reaction is preferably performed in a solution, and toluene, xylene, benzene, and the like are given as a solvent that can be used in the reaction. However, the catalyst, ligand, base, and solvent which can be used are not limited to these examples. In addition, the reaction is more preferably performed under an inert atmosphere of nitrogen, argon, or the like.

When $Ar^1$ in the triarylamine compound represented by the general formula (G1) is represented by the general formula (G1-2), a triarylamine compound represented by a general formula (G') can be synthesized by a synthesis method illustrated in a synthesis scheme (B) illustrated below.

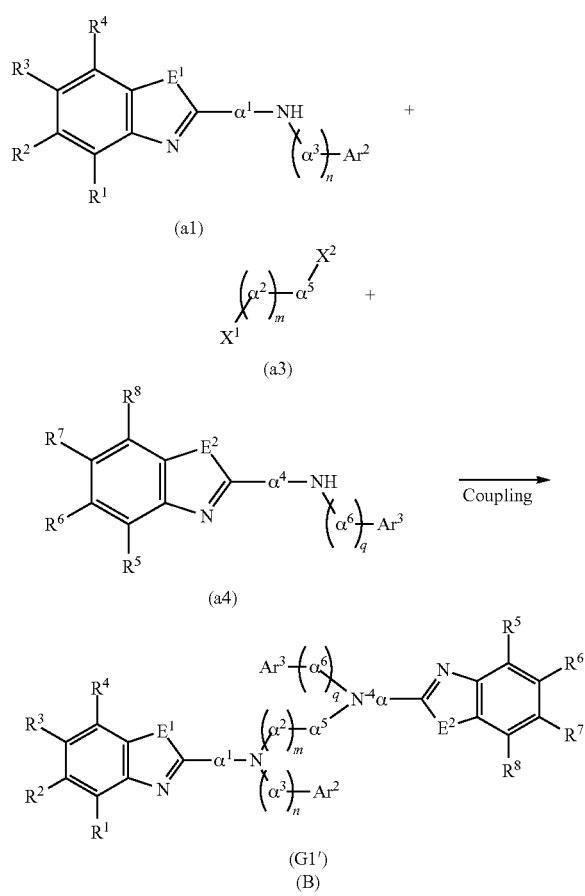

(a1)

(a3)

(a4)

(G1')

(B)

In the formula, $X^1$ and $X^2$ each independently represent halogen. As the halogen, iodine, bromine, and chlorine can facilitate the reaction and are preferred in this order.

As illustrated in the scheme (B), a diarylamine compound (a1), a dihalogenated aryl compound (a3), and a diarylamine compound (a4) undergo coupling, thereby forming a triarylamine compound represented by the above general formula (G1').

Note that there are a variety of reaction conditions for the reaction in the scheme (B). As an example, a synthesis method using a metal catalyst in the presence of a base can be employed.

The case where a Hartwig-Buchwald reaction is used in the above synthesis reaction is described. A palladium catalyst can be used as a metal catalyst, and a mixture of a palladium complex and a ligand thereof can be used as the palladium catalyst. Examples of the palladium catalyst are bis(dibenzylideneacetone)palladium(0), palladium(II) acetate, and the like. Examples of the ligand are tri(tert-butyl)phosphine, tri(n-hexyl)phosphine, tricyclohexylphosphine, 1,1-bis(diphenylphosphino)ferrocene (abbreviation: DPPF), and the like. Examples of a substance which can be used as a base are organic bases such as sodium-tert-butoxide, inorganic bases such as potassium carbonate, and the like. The reaction is preferably performed in a solution, and toluene, xylene, benzene, and the like are given as a solvent that can be used in the reaction. However, the catalyst, ligand, base, and solvent which can be used are not limited to these examples. In addition, the reaction is more preferably performed under an inert atmosphere of nitrogen, argon, or the like.

In the above case, the compound (a1) and the compound (a4) are preferably the same, in which case the synthesis is simplified.

Examples of the method of synthesizing a triarylamine compound of one embodiment of the present invention are described above; however, the present invention is not limited thereto and any other synthesis method may be employed.

Since each of the above triarylamine compounds of one embodiment of the present inventions has an excellent bipolar property, it can be used as a material having a carrier-transport property in a light-emitting element or as a host material in a light-emitting layer of a light-emitting element.

The use of a triarylamine compound of one embodiment of the present invention allows the light-emitting element to have high emission efficiency, and a drive voltage increase of the light-emitting element to be minimized. Further, by the use of such a light-emitting element, a light-emitting device, an electronic device, or a lighting device having low power consumption can be obtained.

Further, a triarylamine compound of one embodiment of the present invention can also be used for an organic thin film solar cell. Specifically, the triarylamine compound can be used for a carrier-transport layer or a carrier-injection layer in an organic thin film solar cell. The triarylamine compound can be used for a charge generation layer by being mixed with an acceptor substance. The triarylamine compound can be photoexcited and hence can be used for a power generation layer.

The structure described in this embodiment can be combined as appropriate with any of the structures described in the other embodiments.

Embodiment 2

In this embodiment, as one embodiment of the present invention, a light-emitting element in which a triarylamine compound described in Embodiment 1 is used for a hole-transport layer is described with reference to FIG. 1.

In a light-emitting element described in this embodiment, as illustrated in FIG. 1, an EL layer 102 including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge-generation layer (E) 116, and the like in addition to the light-emitting layer 113.

By application of a voltage to such a light-emitting element, holes injected from the first electrode 101 side and electrons injected from the second electrode 103 side recombine in the light-emitting layer 113 to raise a substance contained in the light-emitting layer 113 to an excited state. Then, light is emitted when the substance in the excited state returns to the ground state.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer (E) 116 is a layer containing a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

A specific example in which the light-emitting element described in this embodiment is manufactured is described.

As the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), magnesium (Mg), an alkaline earth metal such as calcium (Ca) or strontium (Sr), an alloy containing such an element (MgAg, AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

As the substance having a high hole-transport property used for the hole-injection layer 111, the hole-transport layer 112, and the charge-generation layer (E) 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N'-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. A carbazole compound, such as 4,4'-di(N-carbazolyl)biphenyl (abbreviation: CBP), 1,3,5-tris[4-(N-carbazolyl)phenyl]benzene (abbreviation: TCPB), or 9-[4-(10-phenyl-9-anthracenyl)phenyl]-9H-carbazole (abbreviation: CzPA), or the like can be used. The substances mentioned here are mainly ones that have a hole mobility of $10^{-6}$ cm$^2$/Vs or more. Further, other than these substances, a substance that has a property of transporting more holes than electrons may be used.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

Note that as the substance having a high hole-transport property, it is also possible to use a triarylamine compound of one embodiment of the present invention.

As examples of the acceptor substance that is used for the hole-injection layer 111 and the charge-generation layer (E) 116, a transition metal oxide or an oxide of a metal belonging to any of Group 4 to Group 8 of the periodic table can be given. Specifically, molybdenum oxide is particularly preferable.

In particular, a triarylamine compound of one embodiment of the present invention, which has a bipolar property, can be suitably used for the hole-injection layer 111 and the charge generation layer (E) 116 as a mixture with such an acceptor substance. Alternatively, a bipolar organic compound in which an electron-transport skeleton and a hole-transport skeleton are combined can also be used as a mixture with such an acceptor substance.

The light-emitting layer 113 is a layer containing a light-emitting substance. The light-emitting layer 113 may contain only a light-emitting substance; alternatively, an emission center substance may be dispersed in a host material in the light-emitting layer 113.

There is no particular limitation on materials that can be used as the light-emitting substance and the emission center substance in the light-emitting layer 113, and light emitted from these substances may be either fluorescence or phosphorescence. Examples of the above light-emitting substance or emission center substance include the following substances.

Examples of the substance which emits fluorescence are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4- ylidene)propanedinitrile (abbreviation: BisDCM), and 2-{2, 6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like.

Note that as the substance which emits fluorescence, it is also possible to use a triarylamine compound of one embodiment of the present invention.

Examples of the substance which emits phosphorescence are bis[2-(3',5'-bistrifluoromethylphenyl)pyridinato-N,$C^{2'}$] iridium(III) picolinate (abbreviation: Ir($CF_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato) iridium(III) (abbreviation: Ir(ppy)$_3$), bis(2-phenylpyridinato) iridium(III) acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$ (acac)), bis[2-(2'-benzo[4,5-a]thienyppyridinato-N,$C^{2'}$]iridium(III) (acetylacetonate) (abbreviation: Ir(btp)$_2$ (acac)), bis(1-phenylisoquinolinato-N,$C^{2'}$)iridium(III) acetylacetonate (abbreviation: Ir(piq)$_2$(acac)), (acetylacetonato) bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$ (acac)), 2,3,7,8,12,13,17,18-octaethyl-21H,23H-porphine platinum(II) (abbreviation: PtOEP), tris(1,3-diphenyl-1,3-propanedionato)(monophenanthroline)europium(III) (abbreviation: Eu(DBM)$_3$(Phen)), tris[1-(2-thenoyl)-3,3,3-trifluoroacetonato](monophenanthroline)europium(III) (abbreviation: Eu(TTA)$_3$(Phen)), and the like.

Although there is no particular limitation on a material that can be used as the host material described above, any of the following substances can be used for the host material, for example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc (II) (abbreviation: ZnPBO), and bis[2-(2-benzothiazolyl) phenolato]zinc(II) (abbreviation: ZnBTZ); heterocyclic compounds such as 2-(4-biphenylyl)-5-(4-tert-butyl-phenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: Bphen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be given, and specific examples are 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl) triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p] chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl) diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), and the like. One or more substances having a wider energy gap than the emission center substance described above is preferably selected from these substances and known substances. Moreover, in the case where the emission center substance emits phosphorescence, a substance having triplet excitation energy (energy difference between a ground state and a triplet excited state) which is higher than that of the emission center substance is preferably selected as the host material.

Note that as the material that can be used as the above host material, it is also possible to use a triarylamine compound of one embodiment of the present invention. Since a triarylamine compound of one embodiment of the present invention has a high S1 level, when the triarylamine compound is used as a host material for a substance emitting fluorescence, the substance can be used so as to emit light in the visible region. In addition, since a triarylamine compound of one embodiment of the present invention has a high T1 level, when the triarylamine compound is used as a host material for a substance emitting phosphorescence, the substance can be used so as to emit light having a longer wavelength than green light.

Note that the light-emitting layer 113 may have a structure in which two or more layers are stacked. For example, in the case where the light-emitting layer 113 is formed by stacking a first light-emitting layer and a second light-emitting layer in that order over the hole-transport layer, a substance having a hole-transport property is used for the host material of the first light-emitting layer and a substance having an electron-transport property is used for the host material of the second light-emitting layer.

The electron-transport layer 114 is a layer containing a substance having a high electron-transport property. For the electron-transport layer 114, it is possible to use a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$). It is also possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs). It is also possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly [(9,9-dioctylfluorene-2,7-diyl)-co-(2,2'-bipyridine-6,6'-diyl)] (abbreviation: PF-BPy). The substances mentioned here mainly have an electron mobility of $10^{-6}$ cm$^2$/Vs or more. Note that other than these substances, a substance that has a property of transporting more electrons than holes may be used for the electron-transport layer.

Furthermore, the electron-transport layer is not limited to a single layer and may be a stack of two or more layers containing any of the above substances.

The electron-injection layer 115 is a layer containing a substance having a high electron-injection property. For the electron-injection layer 115, an alkali metal, an alkaline earth metal, or a compound thereof such as lithium fluoride (LiF), cesium fluoride (CsF), calcium fluoride (CaF$_2$), or lithium oxide (LiO$_x$) can be used. Alternatively, a rare earth metal compound such as erbium fluoride (ErF$_3$) can be used. Any of the above substances for forming the electron-transport layer 114 can also be used.

Alternatively, a composite material in which an organic compound and an electron donor (donor) are mixed may be used for the electron-injection layer 115. The electron donor causes electron generation in the organic compound, and thus such a composite material is excellent in an electron-injection property and an electron-transport property. The organic compound here is preferably a material excellent in transporting the generated electrons; specific examples include a substance for forming the electron-transport layer 114 (e.g., a metal complex or a heteroaromatic compound), which is described above. The electron donor is preferably a substance showing an electron-donating property with respect to the organic compound. Specifically, an alkali metal, an alkaline earth metal, and a rare earth metal are preferable, and lithium, cesium, magnesium, calcium, erbium, ytterbium, and the like can be given. Alkali metal oxides or alkaline earth metal oxides are also preferable and examples are lithium oxide, calcium oxide, barium oxide, and the like. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, electron-injection layer 115, and charge-generation layer (E) 116 can be formed by a method such as an evaporation method (e.g., a vacuum evaporation method), an inkjet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element is formed using a triarylamine compound of one embodiment of the present invention for the hole-transport layer, whereby the element efficiency of the light-emitting element can be improved and a drive voltage increase can be minimized.

Since a triarylamine compound of one embodiment of the present invention can be used for not only a hole-transport layer but also other layers (such as a hole-injection layer, a light-emitting layer, and an electron-transport layer), it is possible that a plurality of layers includes the same material. Thus, costs of synthesis of a material or manufacture of a light-emitting element can be reduced, and therefore the use of the triarylamine compound is preferred.

Note that the light-emitting element described in this embodiment is an example of a light-emitting element manufactured using a triarylamine compound of one embodiment of the present invention. The above element structure can be applied to a passive matrix light-emitting device, an active matrix light-emitting device, or the like, and by being partly modified, the element structure can be applied to a light-emitting device with a microcavity structure. The present invention includes all these light-emitting devices. These light-emitting devices can have reduced power consumption.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

Embodiment 3

In this embodiment, as one embodiment of the present invention, a light-emitting element in which two or more kinds of organic compounds as well as a phosphorescent compound are used for a light-emitting layer is described.

Figure 2:
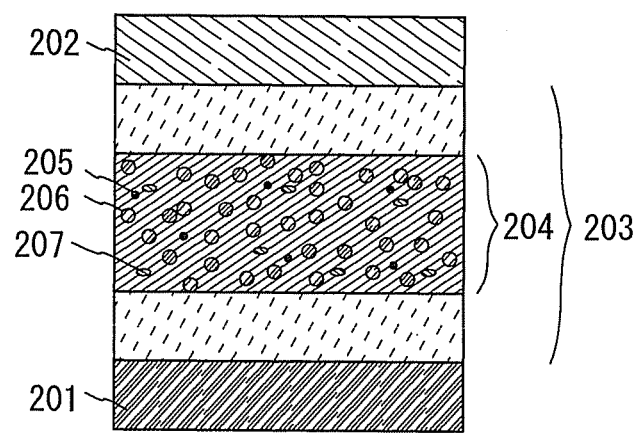
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, a charge-generation layer (E), and the like. Note that for the hole-injection layer, the hole-transport layer, the electron-transport layer, the electron-injection layer, and the charge-generation layer (E), the substances described in Embodiment 2 can be used.

The light-emitting layer 204 described in this embodiment contains a phosphorescent compound 205, a first organic compound 206, and a second organic compound 207. A triarylamine compound described in Embodiment 1 can be used as the first organic compound 206 or the second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level (T1 level) of each of the first organic compound 206 and the second organic compound 207 be higher than that of the phosphorescent compound 205. This is because, when the T1 level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency is decreased.

Here, for improvement in the efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in the case of energy transfer from a singlet excited state, and a phosphorescence spectrum in the case of energy transfer from a triplet excited state) largely overlap with an absorption spectrum of a guest material (specifically, the spectrum of the longest wavelength (lowest energy) absorption band). However, in general, it is difficult to obtain an overlap between a fluorescence spectrum of a host material and the absorption spectrum of the longest wavelength (lowest energy) absorption band of a guest material. The reason for this is as follows: if the fluorescence spectrum of the host material overlaps with the absorption spectrum of the longest wavelength (lowest energy) absorption band of the guest material, since a phosphorescence spectrum of the host material is located on a longer wavelength (lower energy) side as compared to the fluorescence spectrum, the T1 level of the host material becomes lower than the T1 level of the phosphorescent compound and the above-described problem of quenching occurs; yet, when the host material is designed in such a manner that the T1 level of the host material is higher than the T1 level of the phosphorescent compound to avoid the problem of quenching, the fluorescence spectrum of the host material is shifted to the shorter wavelength (higher energy) side, and thus the fluorescence spectrum does not have any overlap with the absorption spectrum of the longest wavelength (lowest energy) absorption band of the guest material. For that reason, in general, it is difficult to obtain an overlap between a fluorescence spectrum of a host material and the longest wavelength (lowest energy) absorption band of a guest material so as to maximize energy transfer from a singlet excited state of the host material.

Thus, in this embodiment, a combination of the first organic compound and the second organic compound preferably forms an exciplex (also referred to as excited complex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound and the second organic compound are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur.

For the phosphorescent compound 205, a phosphorescent organometallic complex is preferably used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

Examples of a phosphorescent organometallic complex include bis[2-(3',5'-bistrifluoromethylphenyl)pyridinato-N, $C^{2'}$]iridium(III)picolinate (abbreviation: Ir($CF_3$ ppy)$_2$(pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III)acetylacetonate (abbreviation: Ir(ppy)$_2$(acac)), tris(acetylacetonato)(monophenanthroline)terbium (III) (abbreviation: Tb(acac)$_3$(Phen)), bis(benzo[h]quinolinato)iridium(III)acetylacetonate (abbreviation: Ir(bzq)$_2$(acac)), bis(2,4-diphenyl-1,3-oxazolato-N,$C^{2'}$)iridium(III)acetylacetonate (abbreviation: Ir(dpo)$_2$(acac)), bis [2-(4'-perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), bis[2-(2'-benzo[4,5-a]thienyl)pyridinato-N,$C^{3'}$]iridium(III)acetylacetonate (abbreviation: Ir(btp)$_2$(acac)), bis(1-phenylisoquinolinato-N,$C^{2'}$)iridium (III)acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)$_2$(acac)), (acetylacetonato)bis(2,3,5-triphenylpyrazinato)iridium(III) (abbreviation: Ir(tppr)$_2$ (acac)), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: Eu(DBM)$_3$(Phen)), tris[1-(2-thenoyl)-3,3,3-trifluoroacetonato](monophenanthroline)europium(III) (abbreviation: Eu(TTA)$_3$(Phen)), and the like.

Examples of the compound which is likely to accept electrons include 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-TTT), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-11).

As the compound which is likely to accept holes, a triarylamine compound of one embodiment of the present invention can be used. Besides, the following examples can be given: 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7- yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N-(3-methylphenyl)-N-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex can be at a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound. Thus, high external quantum efficiency of the light-emitting element can be achieved.

Note that in another structure of the present invention, the light-emitting layer 204 can be formed using a host molecule having a hole-trapping property and a host molecule having an electron-trapping property as the two kinds of organic compounds other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

Note that the light-emitting element described in this embodiment is an example of a light-emitting element manufactured using a triarylamine compound of one embodiment of the present invention. The above element structure can be applied to a passive matrix light-emitting device, an active matrix light-emitting device, or the like, and by being partly modified, the element structure can be applied to a light-emitting device with a microcavity structure. The present invention includes all these light-emitting devices.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

Embodiment 4

In this embodiment, as one embodiment of the present invention, a light-emitting element (hereinafter referred to as tandem light-emitting element) in which a plurality of EL layers and a charge-generation layer interposed therebetween is described.

Figure 3A:
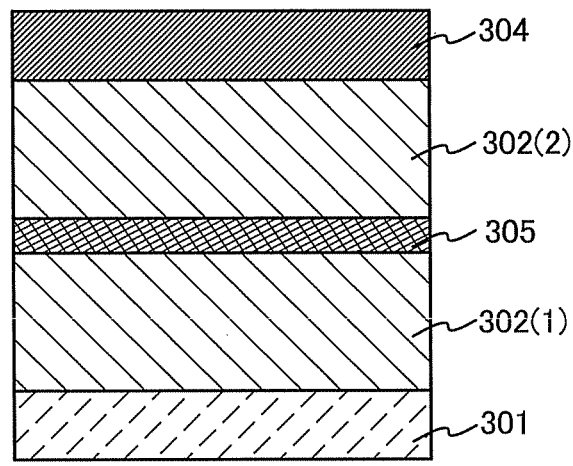
FIGS. 3A and 3B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 2.

In addition, although the plurality of EL layers (the first EL layer 302(1) and the second EL layer 302(2)) may have structures similar to those described in Embodiment 2 or 3, any of the EL layers may have a structure similar to that described in Embodiment 2 or 3. In other words, the structures of the first EL layer 302(1) and the second EL layer 302(2) may be the same or different from each other and can be similar to those described in Embodiment 2 or 3.

Further, a charge-generation layer (I) 305 is provided between the plurality of EL layers (the first EL layer 302(1) and the second EL layer 302(2)). The charge-generation layer (I) 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge-generation layer (I) 305 injects electrons into the first EL layer 302(1) and injects holes into the second EL layer 302(2).

Note that in terms of light extraction efficiency, the charge-generation layer (I) 305 preferably has a light-transmitting property with respect to visible light (specifically, the charge-generation layer (I) 305 has a visible light transmittance of 40% or more). Further, the charge-generation layer (I) 305 functions even if it has lower electric conductivity than the first electrode 301 or the second electrode 304.

The charge-generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. However, another substance may be used as long as the substance is an organic compound having a higher hole-transport property than an electron-transport property. Note that it is also possible to use a triarylamine compound of one embodiment of the present invention as the organic compound having a high hole-transport property in the charge-generation layer (I) 305.

Further, as the electron acceptor, 7,7,8,8-tetracyano-2,3,5, 6-tetrafluoroquinodimethane (abbreviation: $F_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these, molybdenum oxide is especially preferable because it is stable in the air, has a low hygroscopic property, and is easily handled.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, Bphen, BCP, or the like. The substances mentioned here are mainly ones that have an electron mobility of $10^{-6}$ cm$^2$/Vs or higher. Note that another substance may be used as long as the substance is an organic compound having a higher electron-transport property than a hole-transport property.

As the electron donor, it is possible to use an alkali metal, an alkaline earth metal, a rare earth metal, a metal belonging to Group 2 or 13 of the periodic table, or an oxide or carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge-generation layer (I) 305 by using any of the above materials can suppress an increase in drive voltage caused by the stack of the EL layers.

Figure 3B:
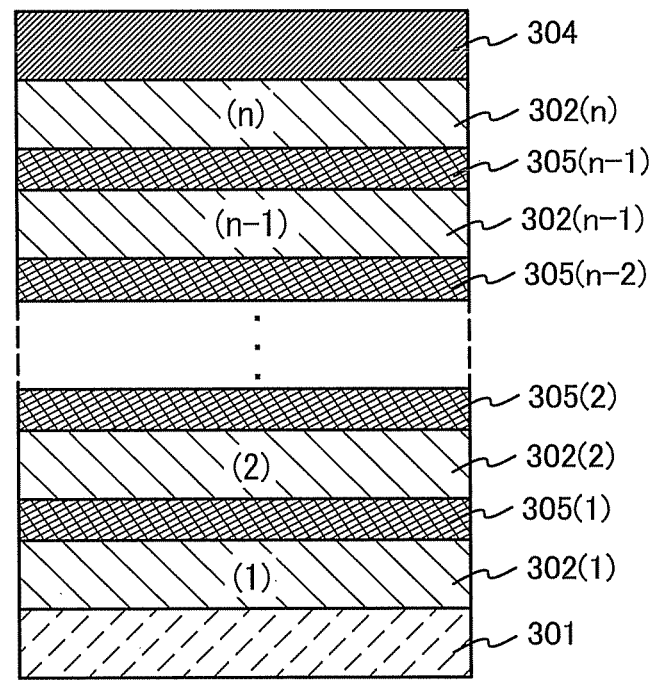

Although this embodiment shows the light-emitting element having two EL layers, the present invention can be similarly applied to a light-emitting element in which n EL layers (302(1) to 302(n)) (n is three or more) are stacked and charge generation layers (I) (305(1) to 305(n-1)) are each provided between these EL layers (302(1) to 302(n)) as illustrated in FIG. 3B. In the case where a plurality of EL layers are included between a pair of electrodes as in the light-emitting element according to this embodiment, by provision of a charge-generation layer (I) between the EL layers, light emission in a high luminance region can be obtained with current density kept low.

Since the current density can be kept low, the element can have a long lifetime. When the light-emitting element is applied for lighting, voltage drop due to resistance of an electrode material can be reduced, thereby achieving homogeneous light emission in a large area. Moreover, it is possible to achieve a light-emitting device of low power consumption, which can be driven at a low voltage.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 5

Figure 4:
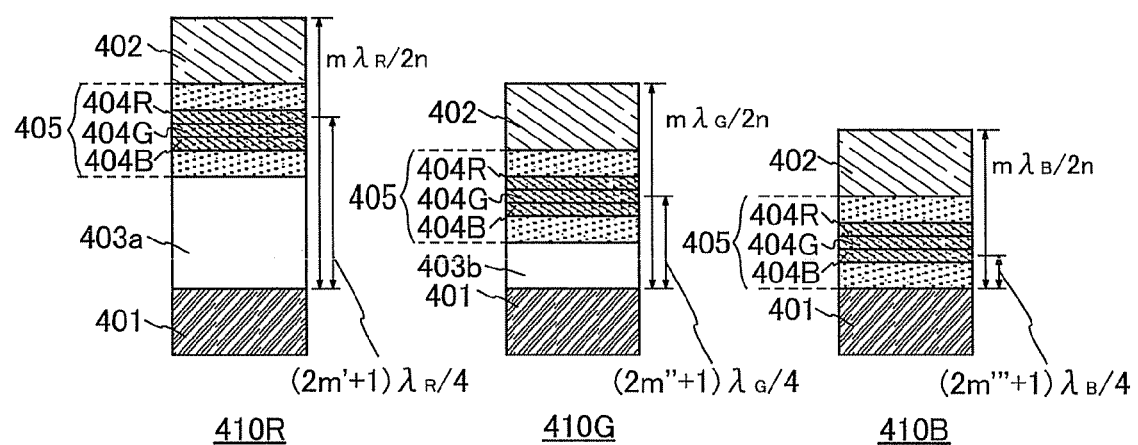
FIG. 4 illustrates a light-emitting device.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge-generation layer (E), and the like. Note that a triarylamine compound of one embodiment of the present invention can be used for any of a hole-injection layer, a hole-transport layer, the light-emitting layer 404, and an electron-transport layer which are included in the EL layer 405.

In this embodiment, a light-emitting device is described which includes light-emitting elements (a first light-emitting element (R) 410R, a second light-emitting element (G) 410G, and a third light-emitting element (B) 410B) having different structures as illustrated in FIG. 4.

The first light-emitting element (R) 410R has a structure in which a first transparent conductive layer 403a; an EL layer 405 including a first light-emitting layer (B) 404B, a second light-emitting layer (G) 404G, and a third light-emitting layer (R) 404R in part; and a semi-transmissive and semi-reflective electrode 402 are sequentially stacked over a reflective electrode 401. The second light-emitting element (G) 410G has a structure in which a second transparent conductive layer 403b, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light ($\lambda_B$) having a peak in a wavelength range from 420 nm to 480 nm. The second light-emitting layer (G) 404G emits light ($\lambda_G$) having a peak in a wavelength range from 500 nm to 550 nm. The third light-emitting layer (R) 404R emits light ($\lambda_R$) having a peak in a wavelength range from 600 nm to 760 nm. Thus, in each of the light-emitting elements (the first light-emitting element (R) 410R, the second light-emitting element (G) 410G, and the third light-emitting element (B) 410B), light emitted from the first light-emitting layer (B) 404B, light emitted from the second light-emitting layer (G) 404G, and light emitted from the third light-emitting layer (R) 404R overlap with each other; accordingly, light having a broad emission spectrum that covers a visible light range can be emitted. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emission in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1\times10^{-2}$ Ωcm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1\times10^{-2}$ Ωcm or lower is used.

In this embodiment, the thicknesses of the transparent conductive layers (the first transparent conductive layer 403*a* and the second transparent conductive layer 403*b*) provided in the first light-emitting element (R) 410R and the second light-emitting element (G) 410G, respectively, are varied between the light-emitting elements, whereby the light-emitting elements differ in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be extracted.

Note that the optical path length (also referred to as optical distance) is expressed as the product of an actual distance and a refractive index, and in this embodiment, is the product of an actual thickness and n (refractive index). That is, an optical path length=actual thickness×n.

Further, the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light ($\lambda_R$) emitted from the third light-emitting layer (R) 404R included in the EL layer 405 is mainly extracted from the first light-emitting element (R) 410R, the light ($\lambda_G$) emitted from the second light-emitting layer (G) 404G included in the EL layer 405 is mainly extracted from the second light-emitting element (G) 410G, and the light ($\lambda_B$) emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402. Hence, the above effect can be assumed to be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness ($(2m'+1)\lambda_R/4$, where m' is a natural number); thus, light emitted from the third light-emitting layer (R) 404R can be amplified. Light (first reflected light) that is reflected by the reflective electrode 401 of the light emission from the third light-emitting layer (R) 404R interferes with light (first incident light) that directly enters the semi-transmissive and semi-reflective electrode 402 from the third light-emitting layer (R) 404R. Therefore, by adjusting the optical path length from the reflective electrode 401 to the third light-emitting layer (R) 404R to the desired value ($(2m'+1)\lambda_R/4$, where m' is a natural number), the phases of the first reflected light and the first incident light can be aligned with each other and the light emission from the third light-emitting layer (R) 404R can be amplified.

Note that, strictly speaking, the optical path length from the reflective electrode 401 to the third light-emitting layer (R) 404R can be the optical path length from a reflection region in the reflective electrode 401 to a light-emitting region in the third light-emitting layer (R) 404R. However, it is difficult to precisely determine the positions of the reflection region in the reflective electrode 401 and the light-emitting region in the third light-emitting layer (R) 404R. Hence, the above effect can be assumed to be sufficiently obtained wherever the reflection region and the light-emitting region may be set in the reflective electrode 401 and the third light-emitting layer (R) 404R, respectively.

Next, in the second light-emitting element (G) 410G, the optical path length from the reflective electrode 401 to the second light-emitting layer (G) 404G is adjusted to a desired thickness ($(2m''+1)\lambda_G/4$, where m'' is a natural number); thus, light emitted from the second light-emitting layer (G) 404G can be amplified. Light (second reflected light) that is reflected by the reflective electrode 401 of the light emission from the second light-emitting layer (G) 404G interferes with light (second incident light) that directly enters the semi-transmissive and semi-reflective electrode 402 from the second light-emitting layer (G) 404G. Therefore, by adjusting the optical path length from the reflective electrode 401 to the second light-emitting layer (G) 404G to the desired value ($(2m''+1)\lambda_G/4$, where m'' is a natural number), the phases of the second reflected light and the second incident light can be aligned with each other and the light emission from the second light-emitting layer (G) 404G can be amplified.

Note that, strictly speaking, the optical path length from the reflective electrode 401 to the second light-emitting layer (G) 404G can be the optical path length from a reflection region in the reflective electrode 401 to a light-emitting region in the second light-emitting layer (G) 404G. However, it is difficult to precisely determine the positions of the reflection region in the reflective electrode 401 and the light-emitting region in the second light-emitting layer (G) 404E Hence, the above effect can be assumed to be sufficiently obtained wherever the reflection region and the light-emitting region may be set in the reflective electrode 401 and the second light-emitting layer (G) 404G, respectively.

Next, in the third light-emitting element (B) 410B, the optical path length from the reflective electrode 401 to the first light-emitting layer (B) 404B is adjusted to a desired thickness $((2m'''+1)\lambda_B/4$, where m''' is a natural number); thus, light emitted from the first light-emitting layer (B) 404B can be amplified. Light (third reflected light) that is reflected by the reflective electrode 401 of the light emission from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value $((2m'''+1)\lambda_B/4$, where m''' is a natural number), the phases of the third reflected light and the third incident light can be aligned with each other and the light emission from the first light-emitting layer (B) 404B can be amplified.

Note that, strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B. Hence, the above effect can be assumed to be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers and a charge-generation layer interposed therebetween are provided in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

Embodiment 6

In this embodiment, a light-emitting device including a light-emitting element in which a triarylamine compound of one embodiment of the present invention is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
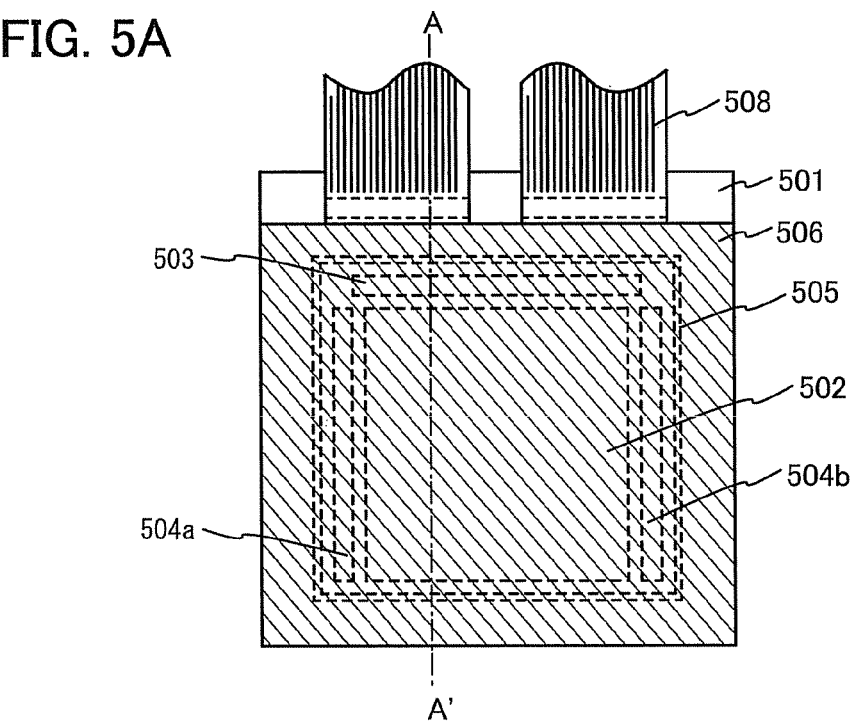
FIGS. 5A and 5B illustrate a light-emitting device.
Figure 5B:
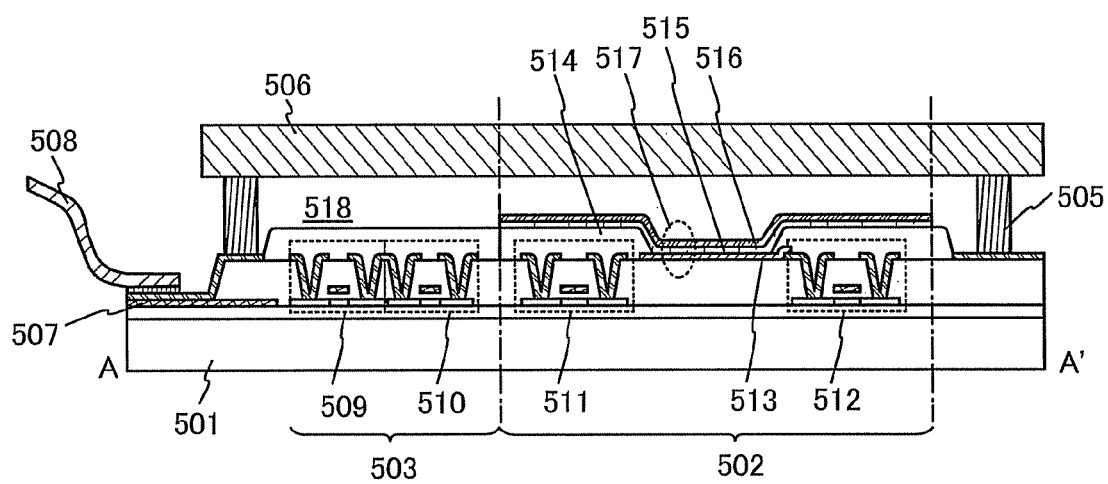

Note that FIG. 5A is a top view illustrating a light-emitting device and FIG. 5B is a cross-sectional view taken along the chain line A-A' in FIG. 5A. The active matrix light-emitting device according to this embodiment includes a pixel portion 502 provided over an element substrate 501, a driver circuit portion (a source line driver circuit) 503, and driver circuit portions (gate line driver circuits) 504a and 504b. The pixel portion 502, the driver circuit portion 503, and the driver circuit portions 504a and 504b are sealed between the element substrate 501 and the sealing substrate 506 by a sealant 505.

In addition, there is provided a lead wiring 507 over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portions 504a and 504b. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and the driver circuit can be formed outside, not over the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 μm to 3 μm) at the upper end portion. Note that the insulator 514 can be formed using either a negative photosensitive material that becomes insoluble in an etchant by light irradiation or a positive photosensitive material that becomes soluble in an etchant by light irradiation. It is possible to use, without limitation to an organic compound, either an organic compound or an inorganic compound such as silicon oxide or silicon oxynitride.

An EL layer 515 and a second electrode (cathode) 516 are stacked over the first electrode (anode) 513. In the EL layer 515, at least a light-emitting layer is provided. Further, in the EL layer 515, a hole-injection layer, a hole-transport layer, an electron-transport layer, an electron-injection layer, a charge-generation layer, and the like can be provided as appropriate in addition to the light-emitting layer. Note that a triarylamine compound of one embodiment of the present invention can be applied to the light-emitting layer, the hole-injection layer, or the hole-transport layer, or the electron-transport layer.

A light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to an FPC 508 which is an external input terminal.

Although the cross-sectional view of FIG. 5B illustrates only one light-emitting element 517, a plurality of light-emitting elements are arranged in matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), polyvinyl fluoride (PVF), polyester, acrylic, or the like can be used.

As described above, an active matrix light-emitting device can be obtained.

Note that the structure described in this embodiment can be combined as appropriate with any of the structures described in the other embodiments.

Embodiment 7

In this embodiment, examples of a variety of electronic devices which are completed using a light-emitting device are described with reference to FIGS. 6A to 6D. The light-emitting device is fabricated using a light-emitting element including a triarylamine compound of one embodiment of the present invention.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 6A to 6D.

FIG. 6A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

FIG. 6B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

FIG. 6C illustrates a portable game machine having two housings, a housing 7301 and a housing 7302, which are connected with a joint portion 7303 so that the portable game machine can be opened or folded. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the light-emitting device is used for at least one of the display portion 7304 and the display portion 7305, and may include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above.

FIG. 6D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 6D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

As described above, the electronic devices can be obtained by the use of the light-emitting device according to one embodiment of the present invention. The light-emitting device has a remarkably wide application range, and can be applied to electronic devices in a variety of fields.

Note that the structure described in this embodiment can be combined as appropriate with any of the structures described in the other embodiments.

Embodiment 8

In this embodiment, examples of lighting devices which are completed using a light-emitting device are described with reference to FIG. 7. The light-emitting device is fabricated using a light-emitting element including a triarylamine compound of one embodiment of the present invention.

Figure 7:
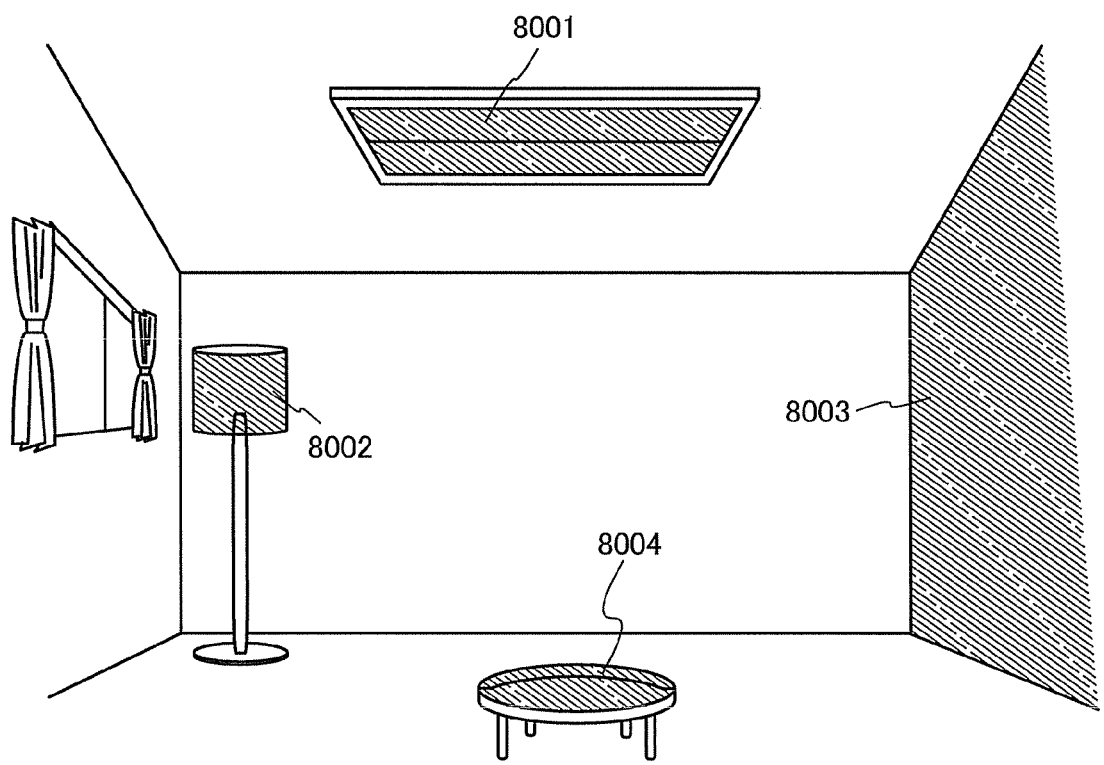
FIG. 7 illustrates lighting devices.

FIG. 7 illustrates an example in which the light-emitting device is used as an indoor lighting device 8001. Since the light-emitting device can have a larger area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

Example 1

Synthesis Example 1

In this example, a method of synthesizing 4-phenyl-4'-(1-phenyl-1H-benzimidazol-2-yl)-phenyl-triphenylamine (abbreviation: BPABIm), which is a triarylamine compound of one embodiment of the present invention represented by the structural formula (100) in Embodiment 1, is described. The structure of BPABIm is shown below.

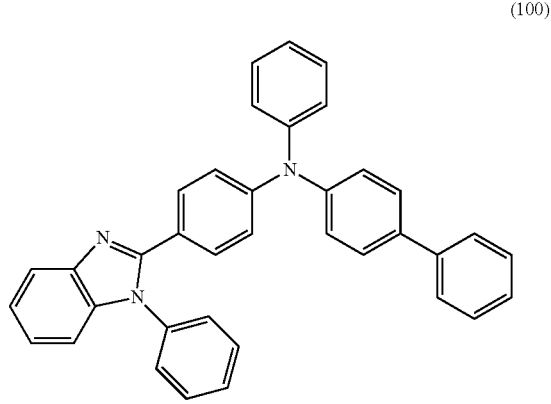 [SMILES: c1ccc(-c2ccc(N(c3ccccc3)c3ccc(-c4nc5ccccc5n4-c4ccccc4)cc3)cc2)cc1]

(100)

Synthesis of 4-Phenyl-4'-(1-phenyl-1H-benzimidazol-2-yl)-phenyl-triphenylamine (abbreviation: BPABIm)

In a 100 mL three-neck flask were put 1.7 g (5.0 mmol) of 2-(4-bromophenyl)-1-phenyl-1H-benzimidazole, 1.2 g (5.0 mmol) of phenyl biphenylamine, 1.0 g (10 mmol) of sodium tert-butoxide, and 17 mg (30 μmol) of bis(dibenzylideneacetone)palladium(0), and the air in the flask was replaced with nitrogen. Then, 10 mL of dehydrated xylene was added to this mixture. After the mixture was deaerated while being stirred under reduced pressure, 200 mL (0.1 mmol) of tri(tert-butyl)phosphine (10 wt % hexane solution) was added thereto. This mixture was stirred under a nitrogen atmosphere at 130° C. for 5 hours to be reacted.

After the reaction, 200 mL of ethyl acetate was added to this reaction mixture, and this suspension was filtered through Florisil and Celite. The obtained filtrate was concentrated and purified by silica gel column chromatography (developing solvent, toluene:ethyl acetate=9:1). The obtained fraction was concentrated, and acetone and methanol were added thereto. The mixture was irradiated with supersonic and then recrystallized, so that the object of the synthesis was obtained as 2.1 g of a light-yellow powder in a yield of 82%.

A reaction scheme of the above synthesis method is illustrated in the following scheme (A-1).

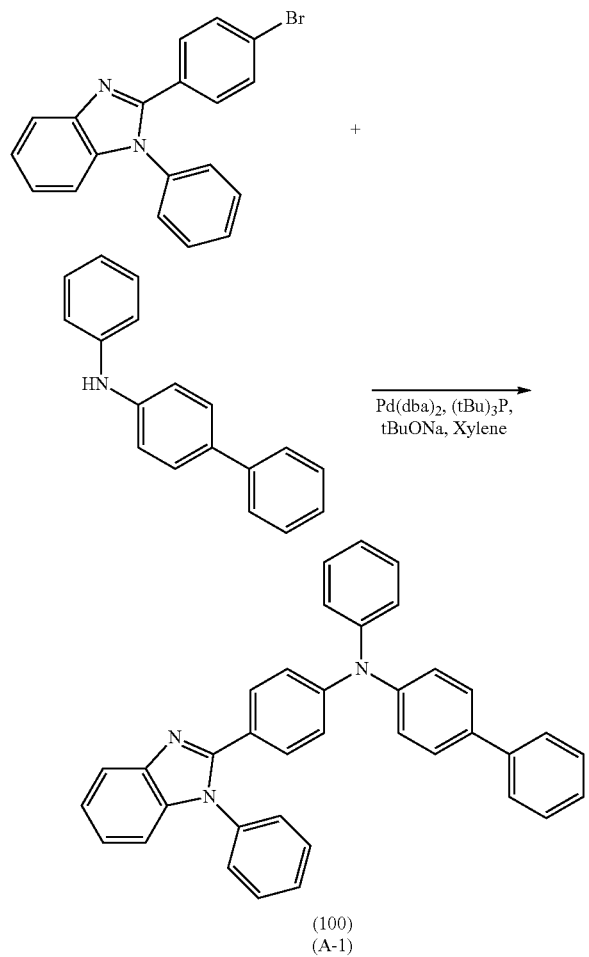

Figure 8A:
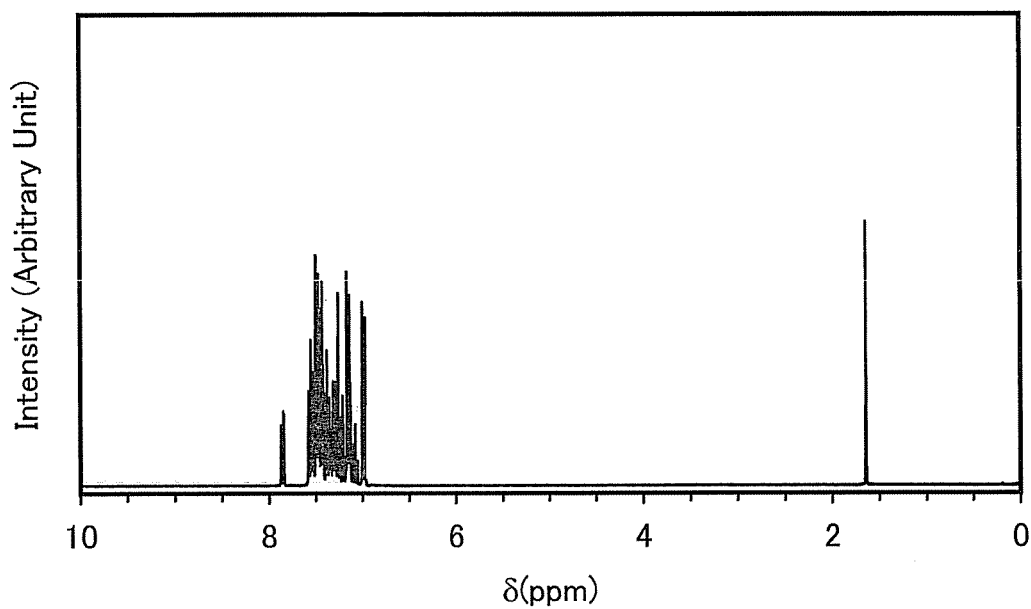
FIGS. 8A and 8B show $^1$H NMR charts of the triarylamine compound represented by the structural formula (100)
Figure 8B:
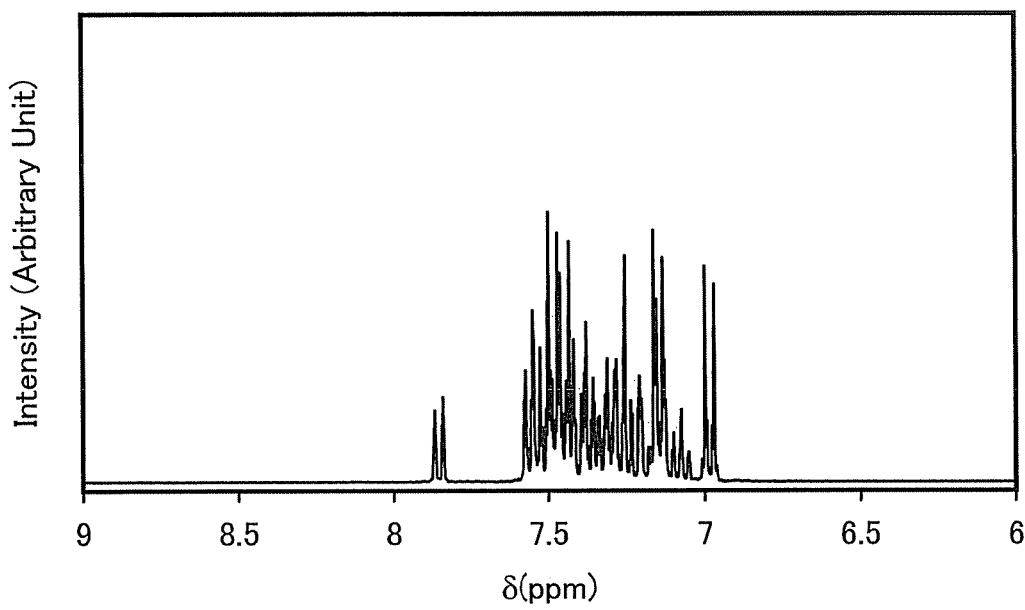

Results of nuclear magnetic resonance spectrometry ($^1$H-NMR), by which the compound obtained by the above synthesis method was analyzed, are shown below. In addition, the $^1$H-NMR charts are shown in FIGS. 8A and 8B. FIG. 8B illustrates an enlarged view within a range of 6 ppm to 9 ppm in FIG. 8A. The results reveal that 4-phenyl-4'-(1-phenyl-1H-benzimidazol-2-yl)-phenyl-triphenylamine (abbreviation: BPABIm), which is the triarylamine compound of one embodiment of the present invention represented by the structural formula (100) shown above, was obtained.

$^1$H NMR (CDCl$_3$, 300 MHz): δ (ppm)=6.98 (d, J=9.0 Hz, 2H), 7.07 (t, J=7.2 Hz, 1H), 7.12-7.58 (m, 25H), 7.85 (d, J=7.8 Hz, 1H).

Next, ultraviolet-visible absorption spectra (hereinafter, simply referred to as "absorption spectra") and emission spectra of BPABIm were measured. The absorption spectra were measured using an ultraviolet-visible light spectrophotometer (V550 type manufactured by Japan Spectroscopy Corporation). The emission spectra were measured using a fluorescence spectrophotometer (FS920 manufactured by Hamamatsu Photonics Corporation). The absorption spectra and the emission spectra of a toluene solution of BPABIm and a thin film of BPABIm were measured. Put in a quartz cell, the toluene solution (0.120 mmol/L) was subjected to the measurement at room temperature. As for the measurement of the absorption spectrum of the thin film, the thin film which was evaporated over a quartz substrate was used and a value obtained by subtraction of an absorption spectrum of quartz from absorption spectra of the thin film and quartz is shown.

Figure 9A:
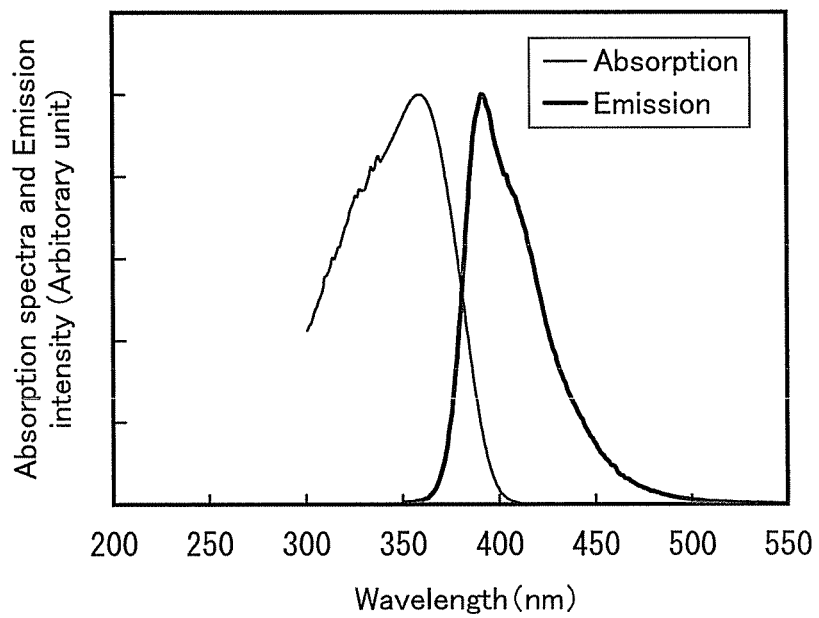
FIGS. 9A and 9B show ultraviolet-visible absorption spectra and emission spectra of the triarylamine compound represented by the structural formula (100)
Figure 9B:
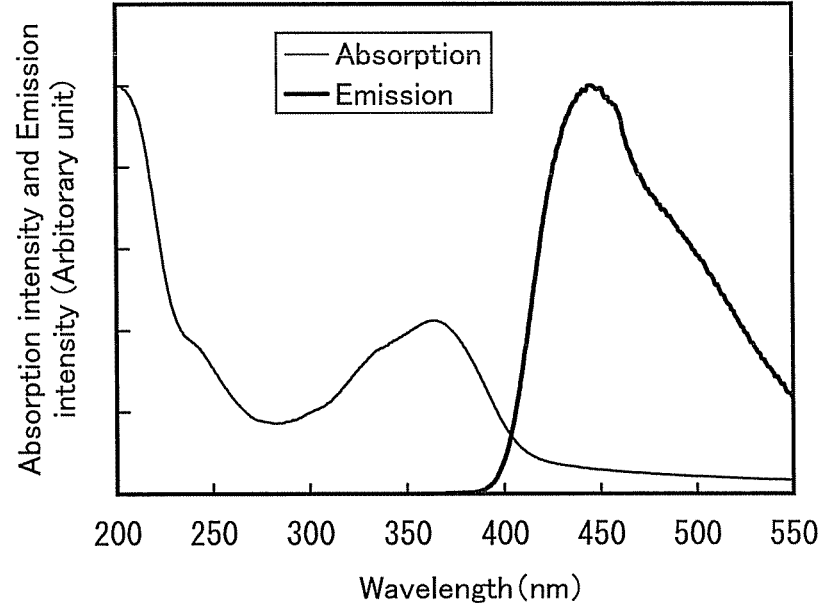

FIGS. 9A and 9B show measurement results of the absorption spectra and emission spectra. FIG. 9A shows the measurement results of the toluene solution of BPABIm. FIG. 9B shows the measurement results of the thin film of BPABIm. In each of FIGS. 9A and 9B, the horizontal axis represents wavelength (nm) and the vertical axis represents absorption intensity (arbitrary unit) or emission intensity (arbitrary unit). In each of FIGS. 9A and 9B, the two solid lines are shown, and the thin line represents absorption spectrum while the thick line represents emission spectrum.

In the case of the toluene solution of BPABIm, an absorption peak is observed at around 361 nm as shown in FIG. 9A. In the case of the thin film of BPABIm, an absorption peak is observed at around 364 nm as shown in FIG. 9B.

Further, in the case of the toluene solution of BPABIm, the maximum emission wavelength is 410 nm (excitation wavelength: 365 nm) as shown in FIG. 9A. In the case of the thin film of BPABIm, the maximum emission wavelength is 445 nm (excitation wavelength: 363 nm) as shown in FIG. 9B.

As described above, BPABIm was found to emit blue light with high color purity and accordingly can be used for a blue light-emitting material.

Further, the HOMO level and the LUMO level of BPABIm were obtained by cyclic voltammetry (CV) measurements. An electrochemical analyzer (ALS model 600A or 600C, manufactured by BAS Inc.) was used for the CV measurements.

Further, as for a solution used for the CV measurements, dehydrated dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. Through the measurements, room temperature (20° C. to 25° C.) and a scan rate of 0.1 V/sec were employed. Note that the potential energy of the reference electrode with respect to the vacuum level was assumed to be −4.94 eV in this example.

On the assumption that the intermediate potential (the half-wave potential) between the oxidation peak potential $E_{pa}$ and the reduction peak potential $E_{pc}$ which are obtained in the CV measurements corresponds to the HOMO level, the HOMO level of BPABIm was calculated at −5.37 eV, and the LUMO level of BPABIm was calculated at −2.28 eV. Accordingly, the band gap (ΔE) of BPABIm was found to be 3.09 eV.

Consequently, BPABIm was found to have a wide band gap.

In addition, the oxidation peak took a similar value even after the 100 cycles. This indicates that BPABIm has characteristics effective against repetitive redox reactions between an oxidation state and a neutral state.

Thus, BPABIm was found capable of favorably transporting holes.

Example 2

Synthesis Example 2

In this example, a method of synthesizing N,N'-diphenyl-N,N'-di-{4-(1,3-benzoxazol-2-yl)-phenyl}benzidine (abbreviation: BOxABP), which is a triarylamine compound of one embodiment of the present invention represented by the structural formula (135) in Embodiment 1, is described. The structure of BOxABP is shown below.

N,N'-diphenylbenzidine, 1.0 g (10 mmol) of sodium tert-butoxide, and 28 mg (50 μmol) of bis(dibenzylideneacetone)palladium(0), and the air in the flask was replaced with nitrogen. Then, 20 mL of dehydrated xylene was added to this mixture. After the mixture was deaerated while being stirred under reduced pressure, 0.3 mL (0.2 mmol) of tri(tert-butyl)phosphine (10 wt % hexane solution) was added thereto. This mixture was stirred under a nitrogen atmosphere at 130° C. for 4.5 hours to be reacted.

After the reaction, 200 mL of ethyl acetate was added to this reaction mixture, and this suspension was filtered through Florisil and Celite. The obtained filtrate was concentrated and purified by silica gel column chromatography (developing solvent, toluene:ethyl acetate=9:1). The obtained fraction was concentrated, and acetone and methanol were added

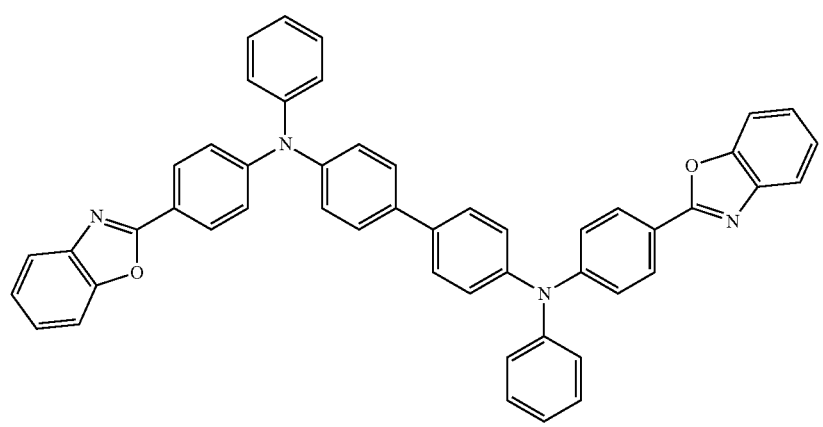

(135)

Synthesis of N,N'-Diphenyl-N,N'-di-{4-(1,3-benzoxazol-2-yl)-phenyl}benzidine (abbreviation: BOxABP)

In a 50 mL three-neck flask were put 1.4 g (5.2 mmol) of 2-(4-bromophenyl)-1,3-benzoxazole, 0.8 g (2.5 mmol) of thereto. The mixture was irradiated with supersonic and then recrystallized, so that the object of the synthesis was obtained as 1.7 g of a yellow powder in a yield of 96%.

A reaction scheme of the above synthesis method is illustrated in the following scheme (B-1).

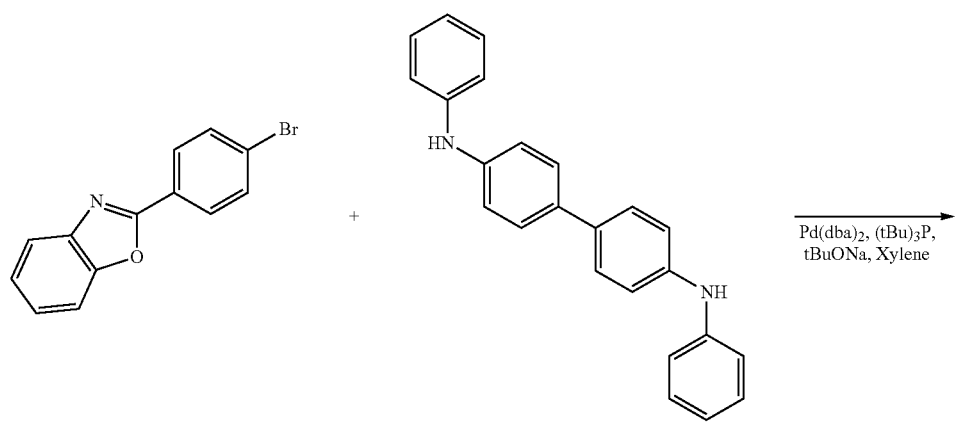

-continued

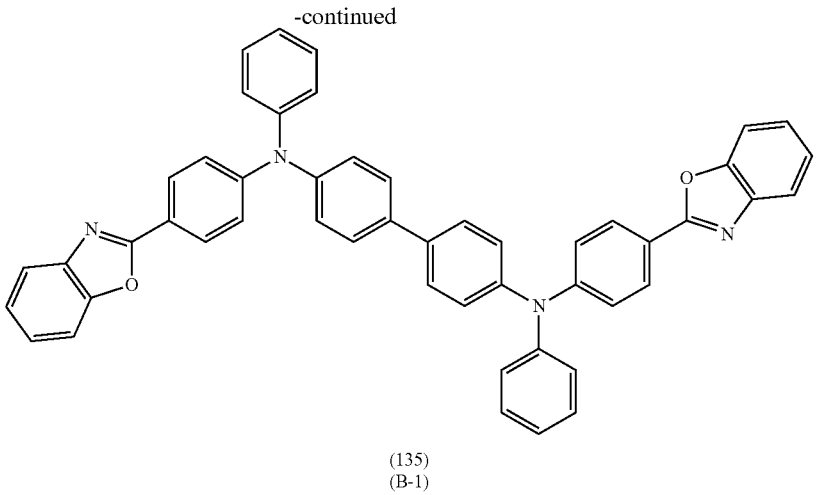

(135)
(B-1)

The Rf values of the object of the synthesis, 2-(4-bromophenyl)-1,3-benzoxazole, and N,N'-diphenylbenzidine were respectively 0.35, 0.67, and 0.30 which were found by silica gel thin layer chromatography (TLC) (developing solvent, ethyl acetate:hexane=1:5).

Figure 10A:
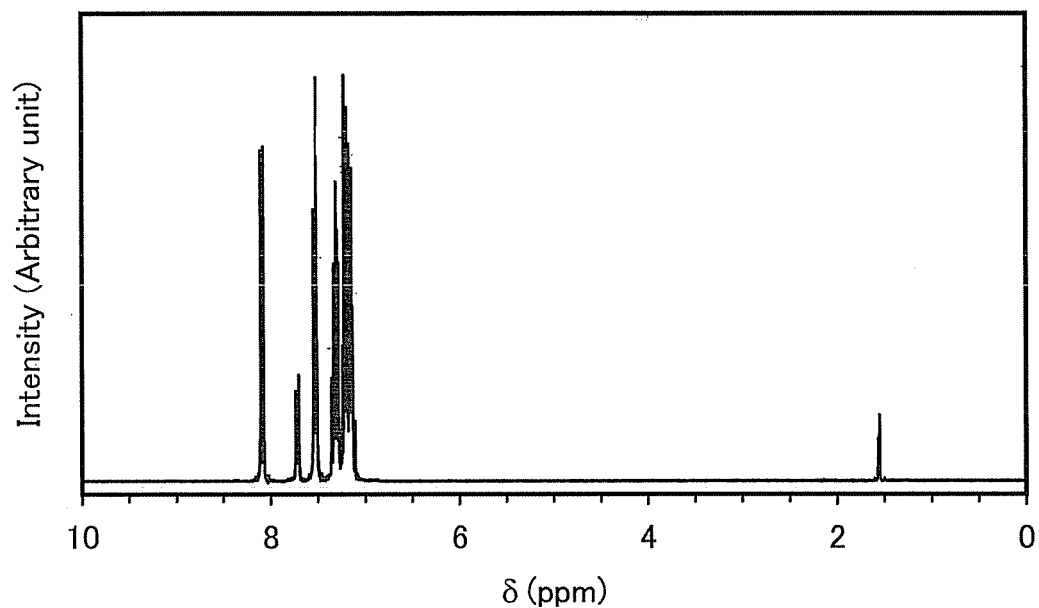
FIGS. 10A and 10B show $^1$H NMR charts of the triarylamine compound represented by the structural formula (135)
Figure 10B:
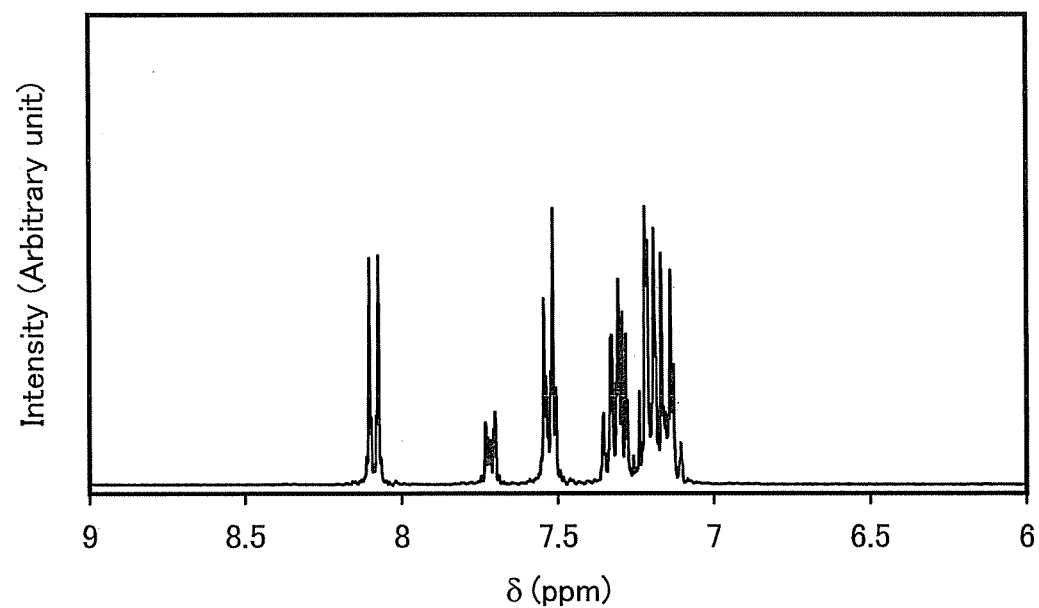

Results of nuclear magnetic resonance spectrometry ($^1$H-NMR), by which the compound obtained by the above synthesis method was analyzed, are shown below. In addition, the $^1$H-NMR charts are shown in FIGS. 10A and 10B. FIG. 10B illustrates an enlarged view within a range of 6 ppm to 9 ppm in FIG. 10A. The results reveal that N,N'-diphenyl-N,N'-di-{4-(1,3-benzoxazol-2-yl)-phenyl}benzidine (abbreviation: BOxABP), which is the triarylamine compound of one embodiment of the present invention represented by the structural formula (135) shown above, was obtained.

$^1$H NMR (CDCl$_3$, 300 MHz): δ (ppm)=7.11-7.24 (m, 14H), 7.28-7.35 (m, 8H), 7.51-7.55 (m, 6H), 7.70-7.73 (m, 2H), 8.90 (d, J=8.7 Hz, 4H).

Next, ultraviolet-visible absorption spectra (hereinafter, simply referred to as "absorption spectra") and emission spectra of BOxABP were measured. The absorption spectra were measured using an ultraviolet-visible light spectrophotometer (V550 type manufactured by Japan Spectroscopy Corporation). The emission spectra were measured using a fluorescence spectrophotometer (FS920 manufactured by Hamamatsu Photonics Corporation). The absorption spectra and the emission spectra of a toluene solution of BOxABP and a thin film of BOxABP were measured. Put in a quartz cell, the toluene solution (0.120 mmol/L) was subjected to the measurements at room temperature. As for the measurements of the absorption spectrum of the thin film, the thin film which was evaporated over a quartz substrate was used and a value obtained by subtraction of an absorption spectrum of quartz from absorption spectra of the thin film and quartz is shown.

Figure 11A:
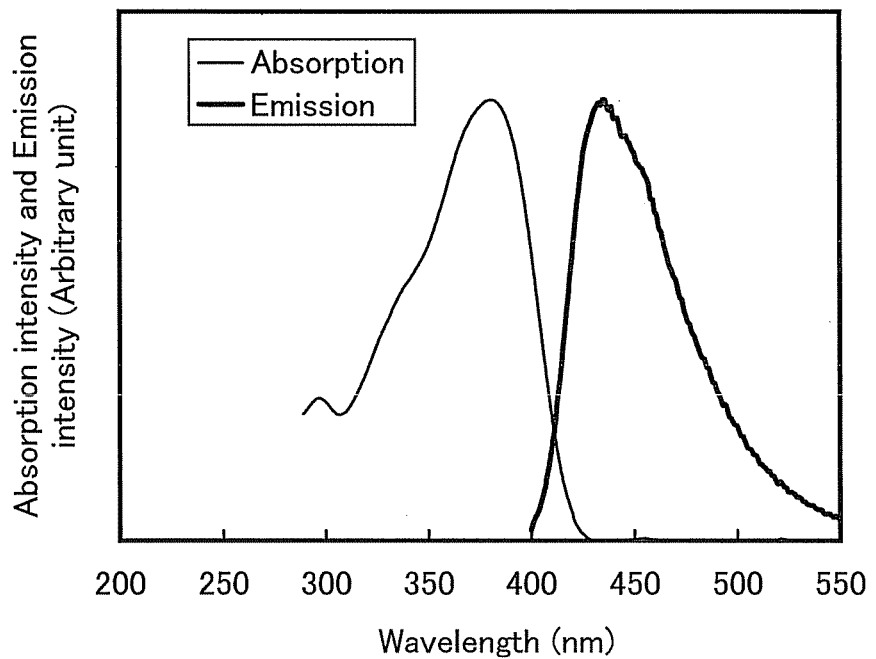
FIGS. 11A and 11B show ultraviolet-visible absorption spectra and emission spectra of the triarylamine compound represented by the structural formula (135)
Figure 11B:
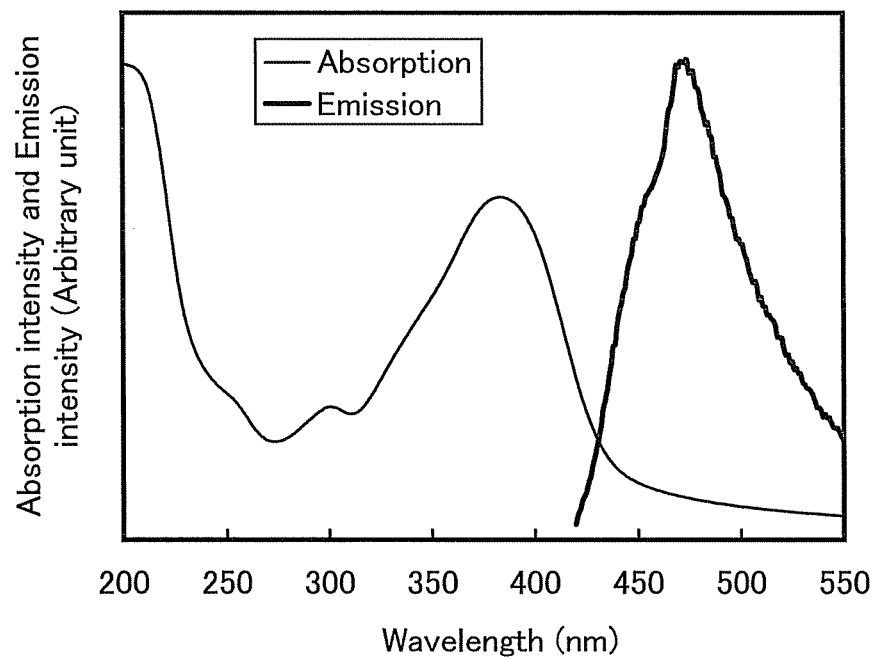

FIGS. 11A and 11B show measurement results of the absorption spectra and emission spectra. FIG. 11A shows the measurement results of the toluene solution of BOxABP. FIG. 11B shows the measurement results of the thin film of BOxABP. In each of FIGS. 11A and 11B, the horizontal axis represents wavelength (nm) and the vertical axis represents absorption intensity (arbitrary unit) or emission intensity (arbitrary unit). In each of FIGS. 11A and 11B, the two solid lines are shown, and the thin line represents absorption spectrum while the thick line represents emission spectrum.

In the case of the toluene solution of BOxABP, an absorption peak is observed at around 381 nm as shown in FIG. 11A. In the case of the thin film of BOxABP, an absorption peak is observed at around 384 nm as shown in FIG. 11B.

Further, in the case of the toluene solution of BOxABP, the maximum emission wavelength is 435 nm (excitation wavelength: 380 nm) as shown in FIG. 11A. In the case of the thin film of BOxABP, the maximum emission wavelength is 472 nm (excitation wavelength: 400 nm) as shown in FIG. 11B.

As described above, BOxABP was found to emit blue light and accordingly can be used for a blue light-emitting material.

Further, the HOMO level and the LUMO level of BOxABP were obtained by cyclic voltammetry (CV) measurements. An electrochemical analyzer (ALS model 600A or 600C, manufactured by BAS Inc.) was used for the CV measurements.

Further, as for a solution used for the CV measurements, dehydrated dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. Through the measurements, room temperature (20° C. to 25° C.) and a scan rate of 0.1 V/sec were employed. Note that the potential energy of the reference electrode with respect to the vacuum level was assumed to be −4.94 eV in this example.

On the assumption that the intermediate potential (the half-wave potential) between the oxidation peak potential $E_{pa}$ and the reduction peak potential $E_{pc}$ which are obtained in the CV measurements corresponds to the HOMO level, the HOMO level of BOxABP was calculated at −5.50 eV, and the LUMO level of BOxABP was calculated at −2.59 eV. Accordingly, the band gap (SE) of BOxABP was found to be 2.91 eV.

Consequently, BOxABP was found to have a wide band gap.

In addition, the oxidation peak took a similar value even after the 100 cycles. This indicates that BOxABP has characteristics effective against repetitive redox reactions between an oxidation state and a neutral state.

Thus, BOxABP was found capable of favorably transporting holes.

Example 3

Figure 12:
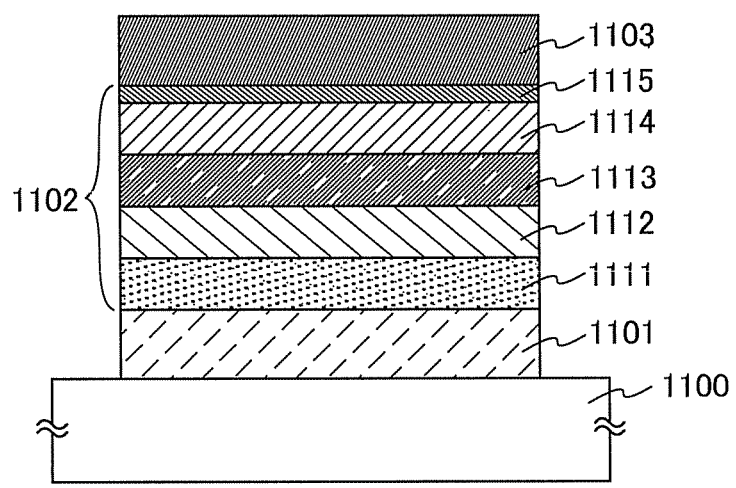
FIG. 12 illustrates a light-emitting element.

In this example is described a light-emitting element 1 in which a triarylamine compound of one embodiment of the present invention, 4-phenyl-4'-(1-phenyl-1H-benzimidazol-2-yl)-phenyl-triphenylamine (abbreviation: BPABIm) (structural formula (100)), was used for a hole-transport layer, with reference to FIG. 12. Chemical formulae of materials used in this example are shown below.

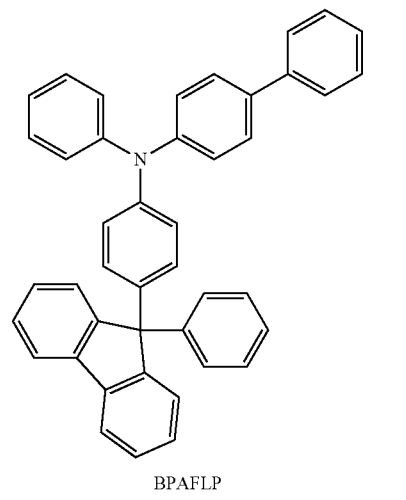

BPAFLP

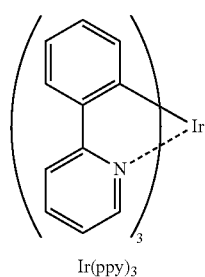

Ir(ppy)$_3$

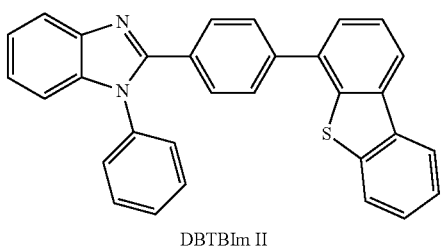

DBTBIm II

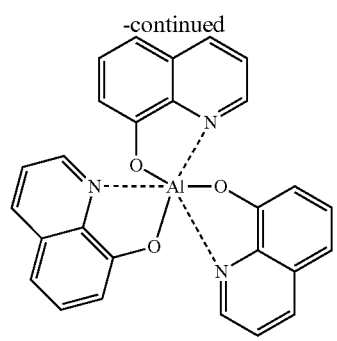

Alq

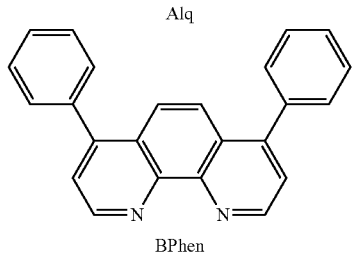

BPhen

Fabrication of Light-Emitting Element 1

First, indium tin oxide containing silicon oxide (ITSO) was deposited over a glass substrate 1100 by a sputtering method, so that a first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that the surface of the substrate 1100 over which the first electrode 1101 was formed faced downward. In this example, a case is described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After the pressure in the vacuum evaporation apparatus was reduced to $10^{-4}$ Pa, 4-phenyl-4'-(9-phenylfluoren-9-yl)triphenylamine (abbreviation: BPAFLP) and molybdenum (VI) oxide were co-evaporated so that the ratio of BPAFLP to molybdenum oxide was 4:2 (mass ratio), thereby forming the hole-injection layer 1111 over the first electrode 1101. The thickness of the hole-injection layer 1111 was set to 50 nm. Note that co-evaporation is an evaporation method in which a plurality of different substances is concurrently vaporized from the respective different evaporation sources.

Then, 4-phenyl-4'-(9-phenylfluoren-9-yl)triphenylamine (abbreviation: BPAFLP) was evaporated to a thickness of 10 nm, so that the hole-transport layer 1112 was formed.

Next, the light-emitting layer 1113 was formed over the hole-transport layer 1112. First, 2-[4-(dibenzothiophen-4-yl)phenyl]-1-phenyl-1H-benzimidazole (abbreviation: DBT- BIm-II), 4-phenyl-4'-(1-phenyl-1H-benzimidazol-2-yl)-phenyl-triphenylamine (abbreviation: BPABIm), and tris(2-phenylpyridinato-N,$C^{2'}$)iridium (abbreviation: Ir(ppy)$_3$) were co-evaporated so that the ratio of DBTBIm-II to BPABIm and Ir(ppy)$_3$ was 1:0.5:0.06 (mass ratio), whereby a 20-nm-thick film was formed. Next, DBTBIm-II and Ir(ppy)$_3$ were co-evaporated so that the ratio of DBTBIm-II to Ir(ppy)$_3$ was 1:0.06 (mass ratio), whereby a 20-nm-thick film was formed. Thus, the light-emitting layer 1113 having a stacked layer structure was formed.

Then, tris(8-quinolinolato)aluminum(III) (abbreviation: Alq) was evaporated to a thickness of 20 nm over the light-emitting layer 1113, thereby forming the electron-transport layer 1114. Furthermore, bathophenanthroline (abbreviation: Bphen) was evaporated to a thickness of 10 nm over the electron-transport layer 1114 and lithium fluoride was then evaporated to a thickness of 1 nm, thereby forming the electron-injection layer 1115.

Lastly, aluminum was evaporated to a thickness of 200 nm over the electron-injection layer 1115 to form the second electrode 1103 serving as a cathode. Thus, the light-emitting element 1 was obtained. Note that in all the above evaporation steps, evaporation was performed by a resistance-heating method.

An element structure of the light-emitting element 1 obtained as described above is shown in Table 1.

Figure 17:
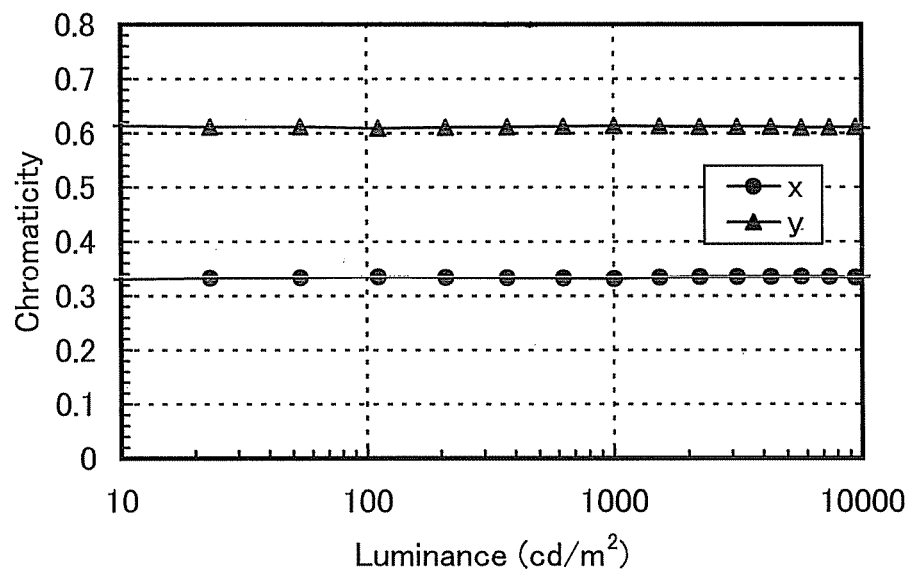
FIG. 17 shows chromaticity versus luminance characteristics of the light-emitting element 1.

16 shows that the drive voltage of the light-emitting element is low. FIG. 17 shows that the light-emitting element exhibits favorable carrier balance at any luminance.

Table 2 below shows initial values of main characteristics of the light-emitting element 1 at a luminance of about 1000 cd/m$^2$.

TABLE 2

|  | Voltage (V) | Current (mA) | Current density (mA/cm$^2$) | Chromaticity coordinates (x, y) | Luminance (cd/m$^2$) | Current efficiency (cd/A) | Power efficiency (lm/W) |
| --- | --- | --- | --- | --- | --- | --- | --- |
| Light-emitting element 1 | 5.0 | 0.07 | 1.7 | (0.33, 0.61) | 1000 | 60 | 38 |

The above results in Table 2 also show that the light-emitting element 1 manufactured in this example has high luminance and high current efficiency. Moreover, as for color purity, the light-emitting element is found to emit green light with excellent color purity.

Figure 18:
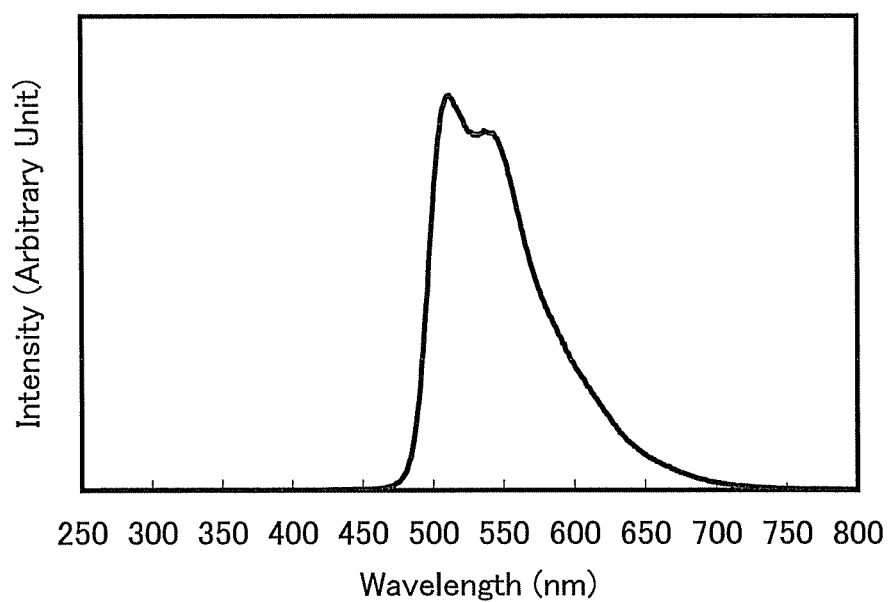
FIG. 18 shows an emission spectrum of the light-emitting element 1.

FIG. 18 shows an emission spectrum when a current at a current density of 25 mA/cm$^2$ was supplied to the light-emitting element 1. FIG. 18 shows that the emission spectrum of the light-emitting element 1 has peaks at around 514 nm and 545 nm, which indicates that the emission spectrum is derived from emission of Ir(ppy)$_3$ included in the light-emitting layer 1113.

Thus, BPABIm has a higher T1 level than a substance which emits green light, and can be used for a host material or a carrier-transport material in a light-emitting element which exhibits fluorescence having a wavelength longer than or equal to that of green light.

TABLE 1

|  | First electrode | Hole-injection layer | Hole-transport layer | Light-emitting layer (1) | Light-emitting layer (2) | Electron-transport layer | Electron-injection layer |  | Second electrode |
| --- | --- | --- | --- | --- | --- | --- | --- | --- | --- |
| Light-emitting element 1 | ITSO (110 nm) | BPAFLP:MoOx (4:2 50 nm) | BPAFLP (10 nm) | * | ** | Alq (20 nm) | Bphen (10 nm) | LiF (1 nm) | Al (200 nm) |

* DBTBIm-II:BPABIm:Ir(ppy)$_3$ (1:0.5:0.06 20 nm)
** DBTBIm-II:Ir(ppy)3 (1:0.06 20 nm)

Further, the manufactured light-emitting element 1 was sealed in a glove box containing a nitrogen atmosphere so as not to be exposed to the air (specifically, a sealant was applied onto an outer edge of the element and heat treatment was performed at 80° C. for 1 hour at the time of sealing).
Operation Characteristics of Light-Emitting Element 1

Operation characteristics of the manufactured light-emitting element 1 were measured. Note that the measurements were carried out at room temperature (under an atmosphere in which the temperature was kept at 25° C.).

Figure 13:
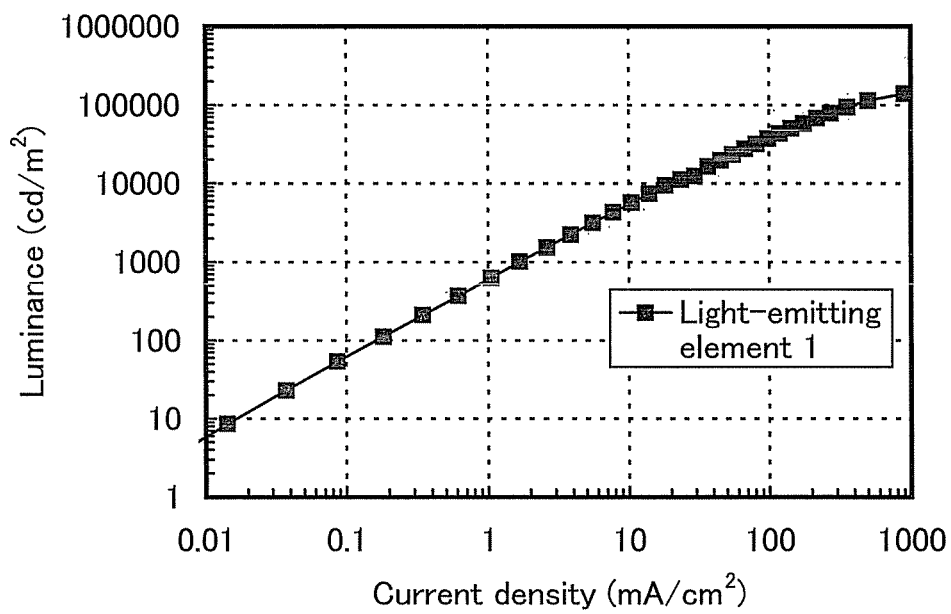
FIG. 13 shows luminance versus current density characteristics of a light-emitting element 1.

FIG. 13 shows luminance versus current density characteristics of the light-emitting element 1. Further, FIG. 14, FIG. 15, FIG. 16, and FIG. 17 show luminance versus voltage characteristics, current efficiency versus luminance characteristics, current versus voltage characteristics, and chromaticity versus luminance characteristics, respectively.

Figure 14:
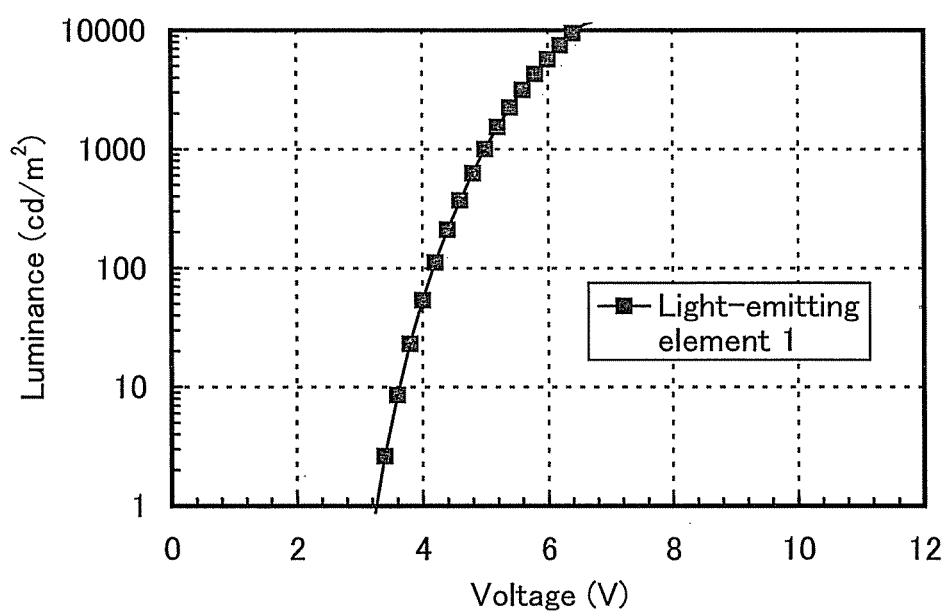
FIG. 14 shows luminance versus voltage characteristics of the light-emitting element 1.
Figure 15:
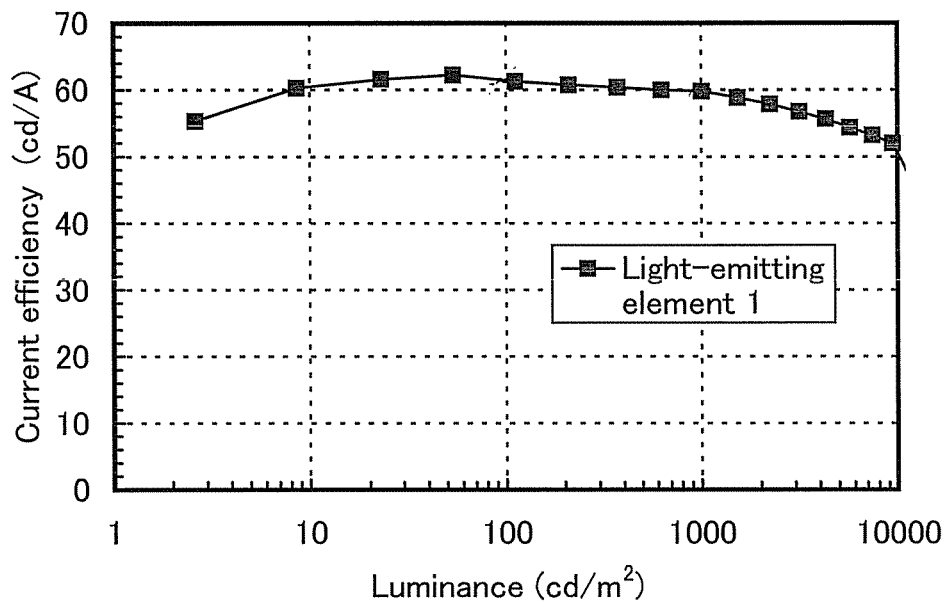
FIG. 15 shows current efficiency versus luminance characteristics of the light-emitting element 1.
Figure 16:
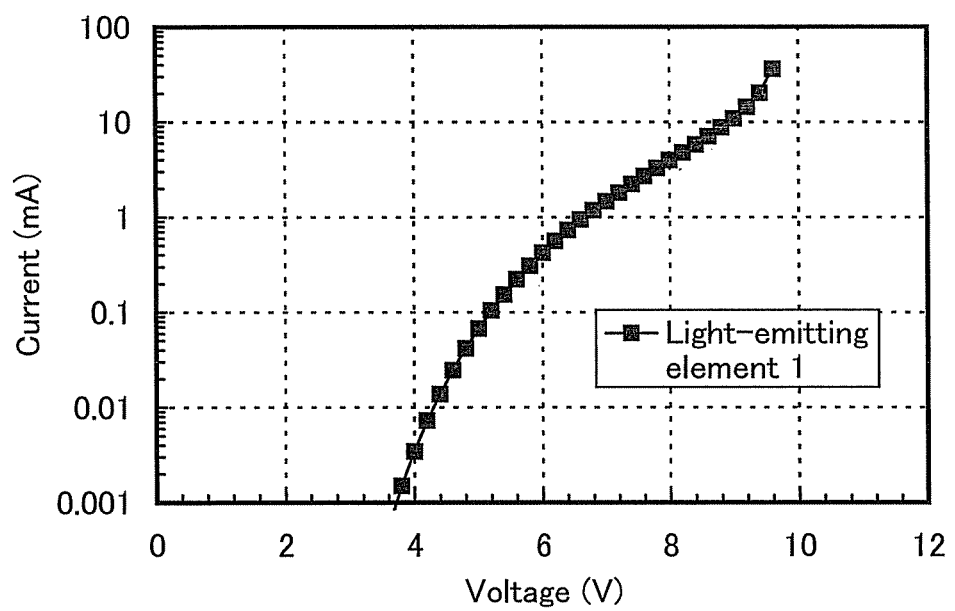
FIG. 16 shows current versus voltage characteristics of the light-emitting element 1.

FIG. 13, FIG. 14 and FIG. 15 show that the light-emitting element 1 in which a triarylamine compound of one embodiment of the present invention was used for the hole-transport layer has low power consumption and high, efficiency. FIG.

Figure 19:
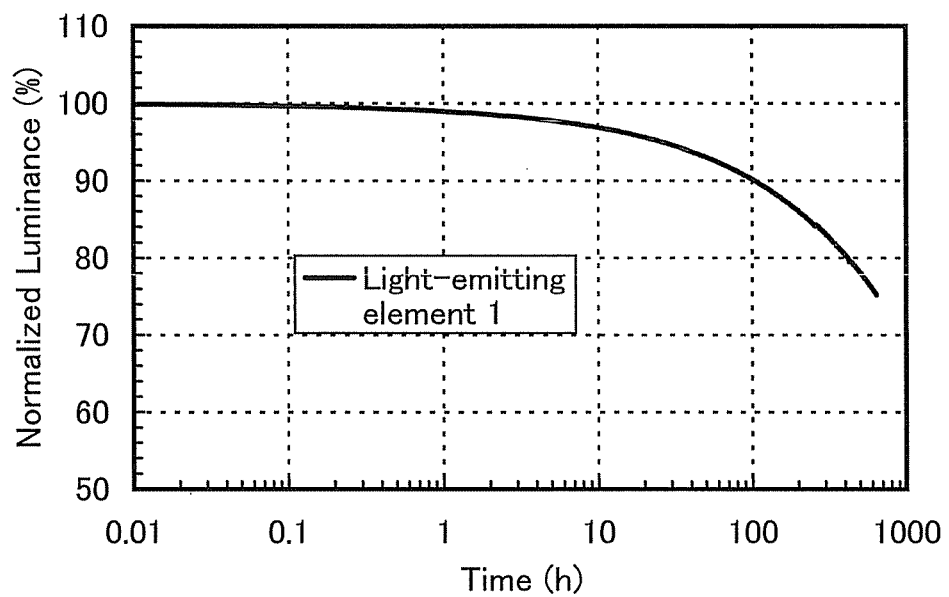
FIG. 19 shows reliability of the light-emitting element 1.

The light-emitting element 1 was subjected to a reliability test. Results of the reliability test are shown in FIG. 19. In FIG. 19, the vertical axis represents normalized luminance (%) with an initial luminance of 100% and the horizontal axis represents driving time (h) of the element. Note that in the reliability test, the light-emitting element 1 was driven under the conditions where the initial luminance was set to 1000 cd/m$^2$ and the current density was constant. According to FIG. 19, the light-emitting element 1 kept about 75% of the initial luminance after 640 hours elapsed. Thus, the reliability test revealed high reliability of the light-emitting element 1. In addition, it was confirmed that, by using a triarylamine compound of one embodiment of the present invention, the light-emitting element can have a long lifetime.

Example 4

In this example are described a light-emitting element 2 in which a triarylamine compound of one embodiment of the present invention, N,N'-diphenyl-N,N'-di-{4-(1,3-benzoxazol-2-yl)-phenyl}benzidine (abbreviation: BOxABP) (structural formula (135)), was used for a hole-transport layer, a light-emitting element 3 in which BOxABP was used for a hole-injection layer, and a light-emitting element 4 in which BOxABP was used for a hole-injection layer and a hole-transport layer. Note that FIG. 12, which is used for explanation of the light-emitting element 1 in Example 1, is used for explanation of the light-emitting elements 2 to 4. Chemical formulae of materials used in this example are shown below.

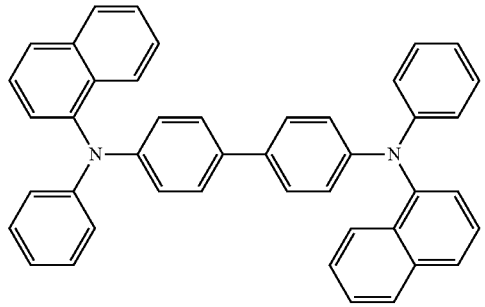

NPB

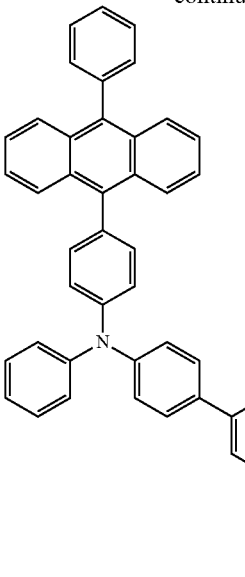

PCBAPA

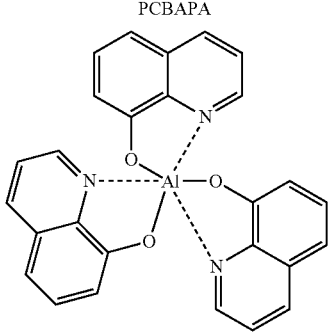

Alq

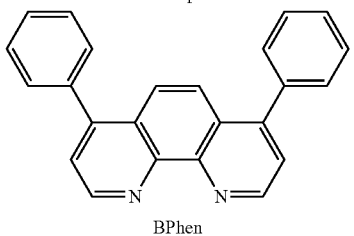

BPhen

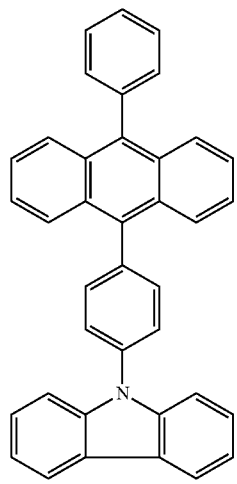

CzPA

Fabrication of Light-Emitting Elements 2 to 4

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Then, as pretreatment for fixating the light-emitting elements over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that the surface of the substrate 1100 over which the first electrode 1101 was formed faced downward. In this example, a case is described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After the pressure in the vacuum evaporation apparatus was reduced to $10^{-4}$ Pa, for the light-emitting element 2, 4,4'-bis[N-(1-naphthyl)-N-phenylamino]biphenyl (abbreviation: NPB) and molybdenum(VI) oxide were co-evaporated so that the ratio of NPB to molybdenum oxide was 4:1 (mass ratio), thereby forming the hole-injection layer 1111 over the first electrode 1101. The thickness of the hole-injection layer 1111 was set to 50 nm. As for the light-emitting elements 3 and 4, BOxABP and molybdenum(VI) oxide were co-evaporated so that the ratio of BOxABP to molybdenum(VI) oxide was 4:1 (mass ratio), thereby forming the hole-injection layer 1111 over the first electrode 1101. The thickness of the hole-injection layer 1111 was set to 50 nm.

For the light-emitting elements 2 and 4, BOxABP was evaporated to a thickness of 10 nm, thereby forming the hole-transport layer 1112. For the light-emitting element 3, NPB was evaporated to a thickness of 10 nm, thereby forming the hole-transport layer 1112.

Co-evaporated were 9-[4-(N-carbazolyl)]phenyl-10-phenylanthracene (abbreviation: CzPA) and 4-(10-phenyl-9-anthryl)-4'-(9-phenyl-9H-carbazol-3-yl)triphenylamine (abbreviation: PCBAPA) so that the ratio of CzPA to PCBAPA was 1:0.1 (mass ratio), thereby forming the light-emitting layer 1113 over the hole-transport layer 1112. The thickness of the light-emitting layer 1113 was set to 30 nm.

Then, tris(8-quinolinolato)aluminum(III) (abbreviation: Alq) was evaporated to a thickness of 10 nm over the light-emitting layer 1113, thereby forming the electron-transport layer 1114. Furthermore, bathophenanthroline (abbreviation: Bphen) was evaporated to a thickness of 20 nm over the electron-transport layer 1114 and lithium fluoride was then evaporated to a thickness of 1 nm, thereby forming the electron-injection layer 1115.

Lastly, aluminum was evaporated to a thickness of 200 nm over the electron-injection layer 1115 to form the second electrode 1103 serving as a cathode. Thus, the light-emitting elements 2 to 4 were obtained. Note that in all the above evaporation steps, evaporation was performed by a resistance-heating method.

An element structure of the light-emitting elements 2 to 4 obtained as described above is shown in Table 3.

TABLE 3

|  | First electrode | Hole-injection layer | Hole-transport layer | Light-emitting layer | Electron-transport layer | Electron-injection layer |  | Second electrode |
|---|---|---|---|---|---|---|---|---|
| Light-emitting element 2 | ITSO (110 nm) | NPB:MoOx (4:1 50 nm) | BOxABP (10 nm) | * | Alq (10 nm) | Bphen (20 nm) | LiF (1 nm) | Al (200 nm) |
| Light-emitting element 3 | ITSO (110 nm) | BOxABP:MoOx (4:1 50 nm) | NPB (10 nm) | * | Alq (10 nm) | Bphen (20 nm) | LiF (1 nm) | Al (200 nm) |
| Light-emitting element 4 | ITSO (110 nm) | BOxABP:MoOx (4:1 50 nm) | BOxABP (10 nm) | * | Alq (10 nm) | Bphen (20 nm) | LiF (1 nm) | Al (200 nm) |

* CzPA:PCBAPA (1:0.1 30 nm)

Further, the manufactured light-emitting elements 2 to 4 were sealed in a glove box containing a nitrogen atmosphere so as not to be exposed to the air (specifically, a sealant was applied onto an outer edge of each element and heat treatment was performed at 80° C. for 1 hour at the time of sealing).

Operation Characteristics of Light-Emitting Elements 2 to 4

Operation characteristics of the manufactured light-emitting elements 2 to 4 were measured. Note that the measurements were carried out at room temperature (under an atmosphere in which the temperature was kept at 25° C.).

Figure 20:
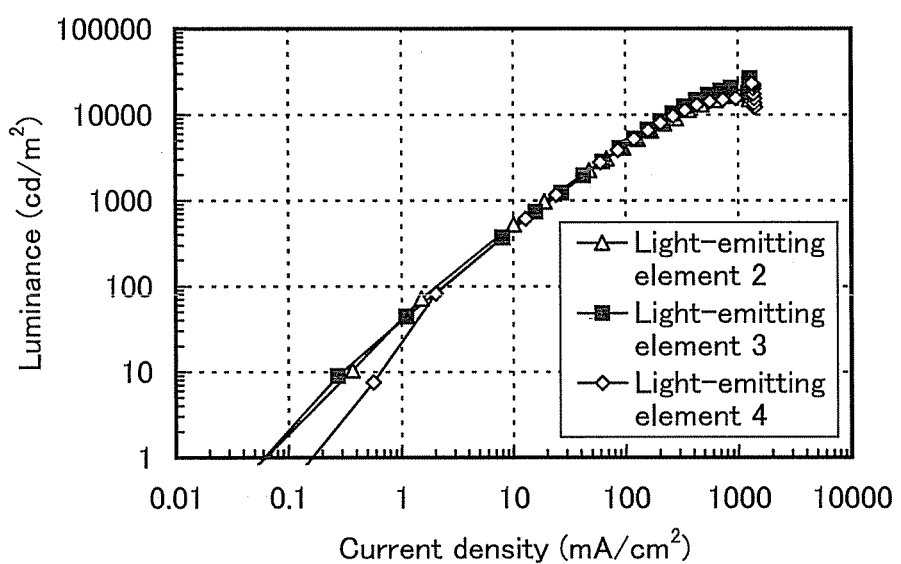
FIG. 20 shows luminance versus current density characteristics of light-emitting elements 2 to 4.

FIG. 20 shows luminance versus current density characteristics of the light-emitting elements 2 to 4. Further, FIG. 21, FIG. 22, and FIG. 23 show luminance versus voltage characteristics, current efficiency versus luminance characteristics, and current versus voltage characteristics, respectively.

Figure 21:
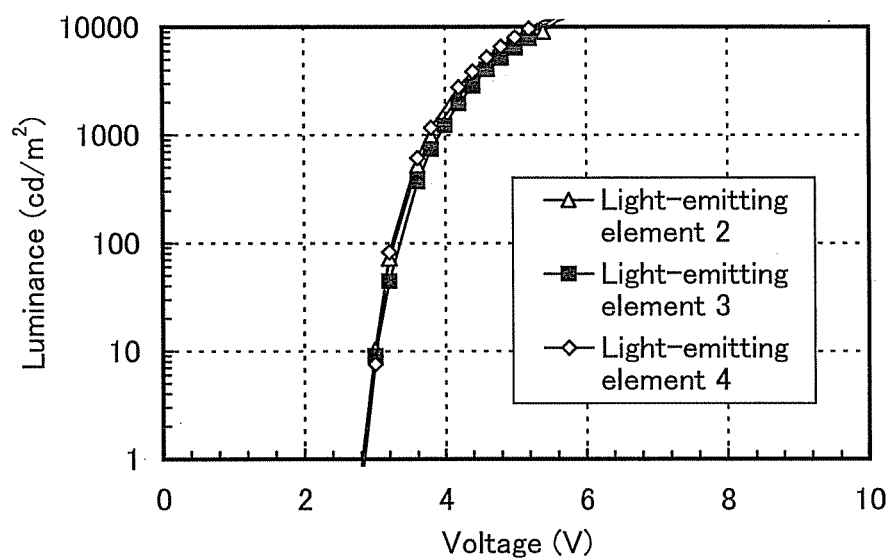
FIG. 21 shows luminance versus voltage characteristics of the light-emitting elements 2 to 4.
Figure 22:
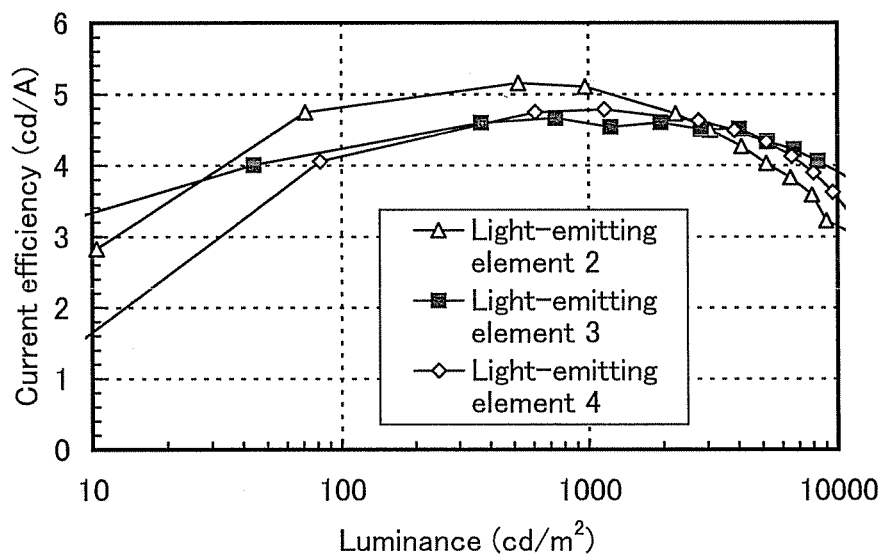
FIG. 22 shows current efficiency versus luminance characteristics of the light-emitting elements 2 to 4.
Figure 23:
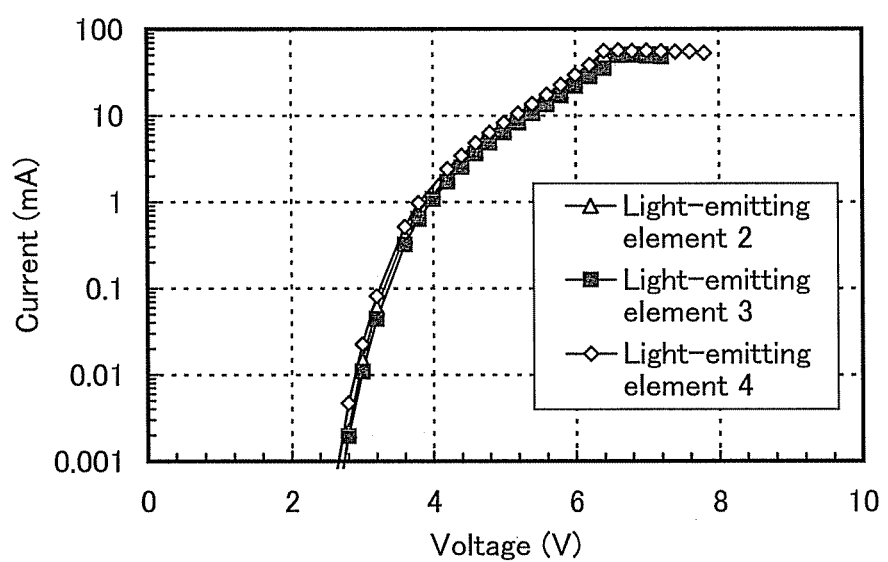
FIG. 23 shows current versus voltage characteristics of the light-emitting elements 2 to 4.

FIG. 20, FIG. 21 and FIG. 22 show that each of the light-emitting elements 2 to 4 in which a triarylamine compound of one embodiment of the present invention was used has low power consumption and high efficiency. FIG. 23 shows that the drive voltage of each light-emitting element is low.

Table 4 below shows initial values of main characteristics of the light-emitting elements 2 to 4 at a luminance of about 1000 cd/m².

TABLE 4

|  | Voltage (V) | Current (mA) | Current density (mA/cm²) | Chromaticity coordinates (x, y) | Luminance (cd/m²) | Current efficiency (cd/A) | Power efficiency (lm/W) |
|---|---|---|---|---|---|---|---|
| Light-emitting element 2 | 3.8 | 0.76 | 19 | (0.16, 0.21) | 970 | 5.1 | 43 |
| Light-emitting element 3 | 3.8 | 0.63 | 16 | (0.16, 0.22) | 740 | 4.7 | 43 |
| Light-emitting element 4 | 3.8 | 0.97 | 24 | (0.16, 0.23) | 1200 | 4.8 | 43 |

The above results in Table 4 also show that the light-emitting elements 2 to 4 manufactured in this example have high luminance and high current efficiency.

Figure 24:
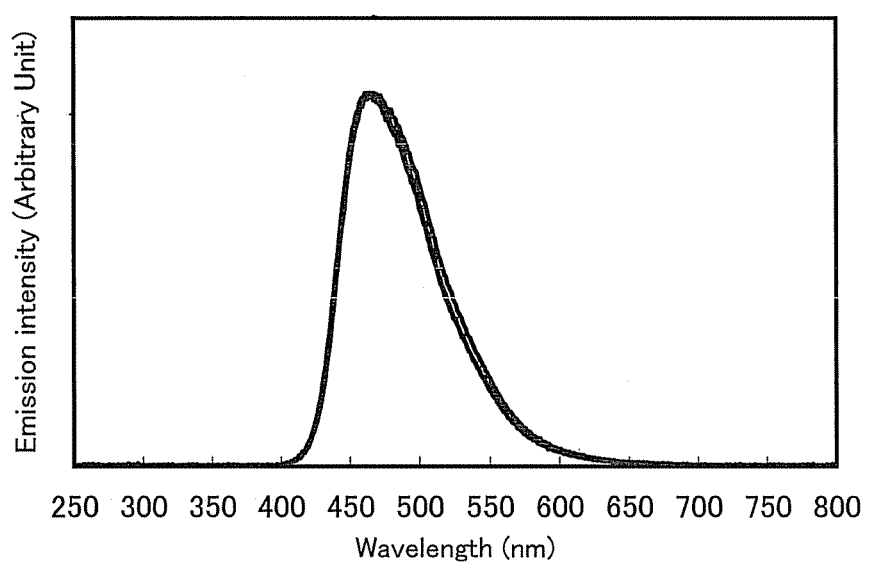
FIG. 24 shows emission spectra of the light-emitting elements 2 to 4.

FIG. 24 shows an emission spectrum when a current at a current density of 25 mA/cm² was supplied to the light-emitting elements 2 to 4. FIG. 24 shows that the emission spectra of the light-emitting elements 2 to 4 have a peak at around 470 nm, which indicates that the emission spectra are derived from emission of PCBAPA included in the light-emitting layer 1113.

The light-emitting element 3 was subjected to a reliability test. Note that in the reliability test, the light-emitting element 3 was driven under the conditions where the initial luminance was set to 1000 cd/m² and the current density was constant. The light-emitting element 3 kept about 79% of the initial luminance after 550 hours elapsed. Thus, the reliability test revealed high reliability of the light-emitting element 3 in which a triarylamine compound of one embodiment of the present invention is used for the hole-injection layer. In addition, it was confirmed that, by using the triarylamine compound of one embodiment of the present invention, the light-emitting element can have a long lifetime.

Example 5

In this example is described a light-emitting element 5 in which a triarylamine compound of one embodiment of the present invention, N,N'-diphenyl-N,N'-di-{4-(1,3-benzoxazol-2-yl)-phenyl}benzidine (abbreviation: BOxABP) (structural formula (135)), was used for a light-emitting layer. Note that FIG. 12, which is used for explanation of the light-emitting element 1 in Example 1, is used for explanation of the light-emitting element 5. Chemical formulae of materials used in this example are shown below.

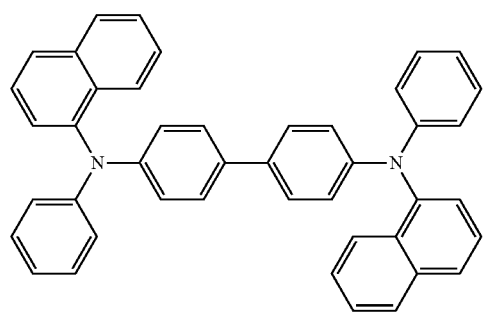

NPB

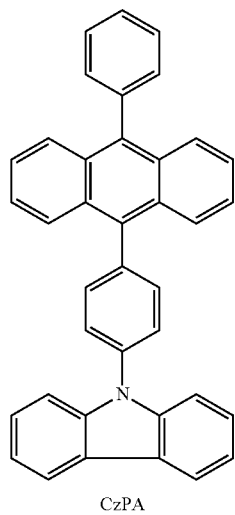

CzPA

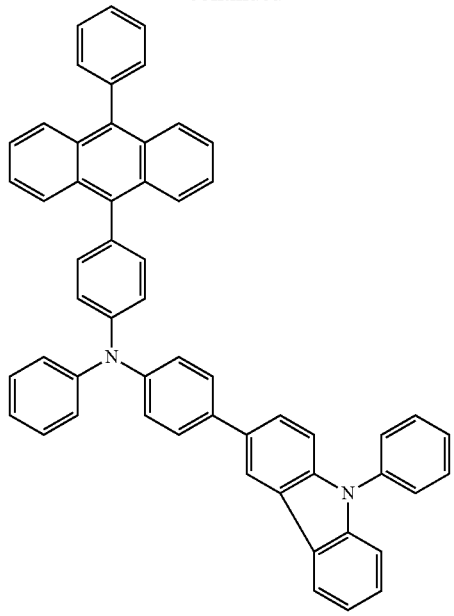

PCBAPA

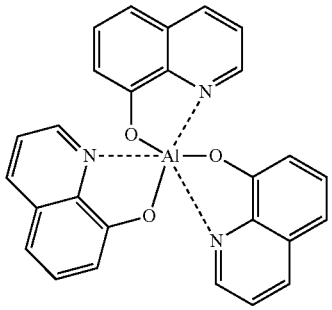

Alq

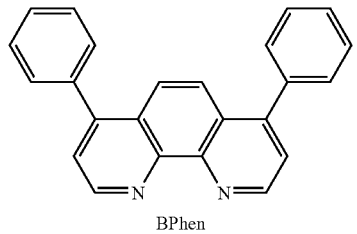

BPhen

Fabrication of Light-Emitting Element 5

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that the surface of the substrate 1100 over which the first electrode 1101 was formed faced downward. In this example, a case is described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After reducing the pressure of the vacuum evaporation apparatus to $10^{-4}$ Pa, 4,4'-bis[N-(1-naphthyl)-N-phenylamino]biphenyl (abbreviation: NPB) and molybdenum(VI) oxide were co-evaporated with a mass ratio of NPB to molybdenum oxide being 4:1, whereby the hole-injection layer 1111 was formed over the first electrode 1101. The thickness of the hole-injection layer 1111 was set to 50 nm.

Next, NPB was evaporated to a thickness of 10 nm, and then 4-(10-phenyl-9-anthryl)-4'-(9-phenyl-9H-carbazol-3-yl)triphenylamine (abbreviation: PCBAPA) was evaporated to a thickness of 30 nm, thereby forming the hole-transport layer 1112.

Next, the light-emitting layer 1113 was formed over the hole-transport layer 1112. Co-evaporated were 9-[4-(10-phenyl-9-anthryl)phenyl]-9H-carbazole (abbreviation: CzPA), BOxABP, and PCBAPA, so that the ratio of CzPA to BOxABP and PCBAPA was 1:0.05:0.1 (mass ratio), thereby forming the light-emitting layer 1113. The thickness of the light-emitting layer 1113 was set to 30 nm.

Then, tris(8-quinolinolato)aluminum(III) (abbreviation: Alq) was evaporated to a thickness of 10 nm over the light-emitting layer 1113, thereby forming the electron-transport layer 1114. Furthermore, lithium fluoride was then evaporated to a thickness of 1 nm over the electron-transport layer 1114, thereby forming the electron-injection layer 1115.

Lastly, aluminum was evaporated to a thickness of 200 nm over the electron-injection layer 1115 to form the second electrode 1103 serving as a cathode. Thus, the light-emitting element 5 was obtained. Note that in all the above evaporation steps, evaporation was performed by a resistance-heating method.

An element structure of the light-emitting element 5 obtained as described above is shown in Table 5.

TABLE 5

| | First electrode | Hole-injection layer | Hole-transport layer | | Light-emitting layer | Electron-transport layer | | Electron-injection layer | Second electrode |
|---|---|---|---|---|---|---|---|---|---|
| Light-emitting element 5 | ITSO (110 nm) | * | NPB (10 nm) | PCBAPA (30 nm) | ** | Alq (30 nm) | Bphen (20 nm) | LiF (1 nm) | Al (200 nm) |

* NPB:MoOx (4:1 50 nm)
** CzPA:BOxABP:PCBAPA (1:0.05:0.1 30 nm)

Further, the manufactured light-emitting element 5 was sealed in a glove box containing a nitrogen atmosphere so as not to be exposed to the air (specifically, a sealant was applied onto an outer edge of the element and heat treatment was performed at 80° C. for 1 hour at the time of sealing).

Operation Characteristics of Light-emitting Element 5

Operation characteristics of the manufactured light-emitting element 5 were measured. Note that the measurements were carried out at room temperature (under an atmosphere in which the temperature was kept at 25° C.).

Figure 25:
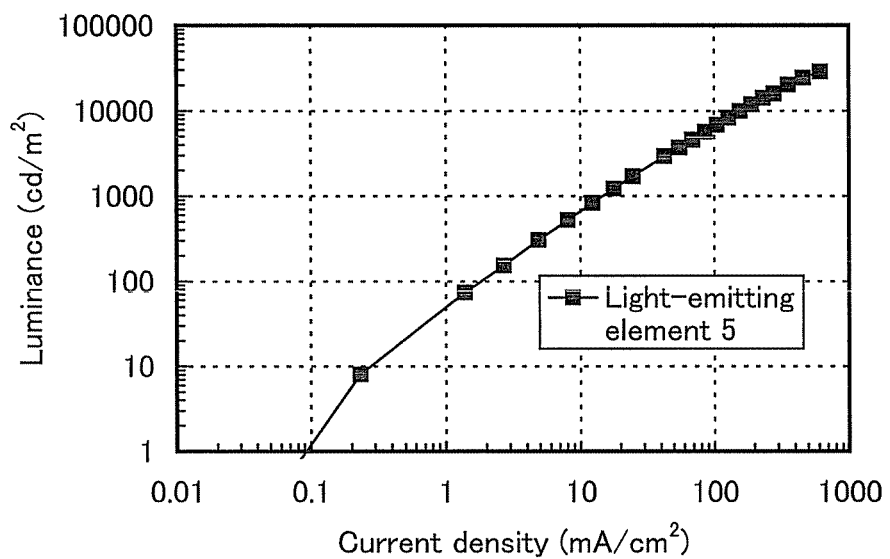
FIG. 25 shows luminance versus current density characteristics of a light-emitting element 5.

FIG. 25 shows luminance versus current density characteristics of the light-emitting element 5. Further, FIG. 26, FIG. 27, and FIG. 28 show luminance versus voltage characteristics, current efficiency versus luminance characteristics, and current versus voltage characteristics, respectively.

Figure 26:
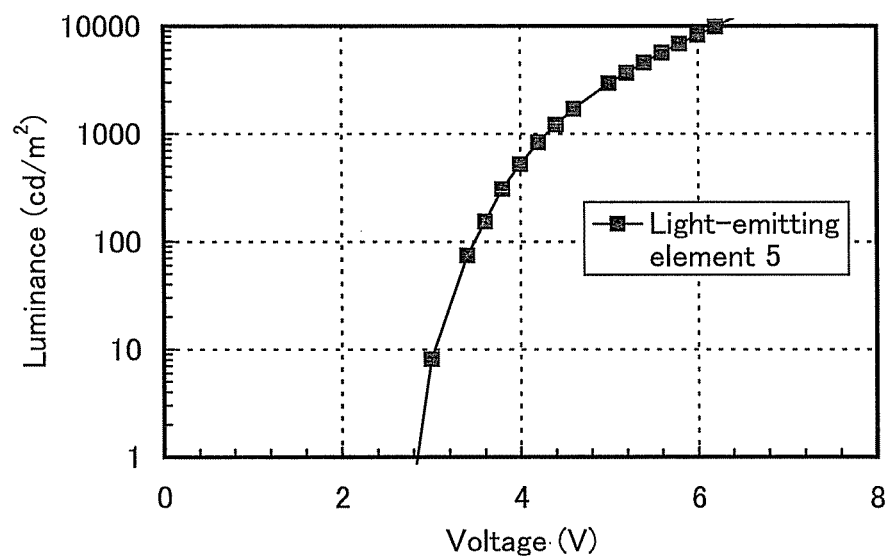
FIG. 26 shows luminance versus voltage characteristics of the light-emitting element 5.
Figure 27:
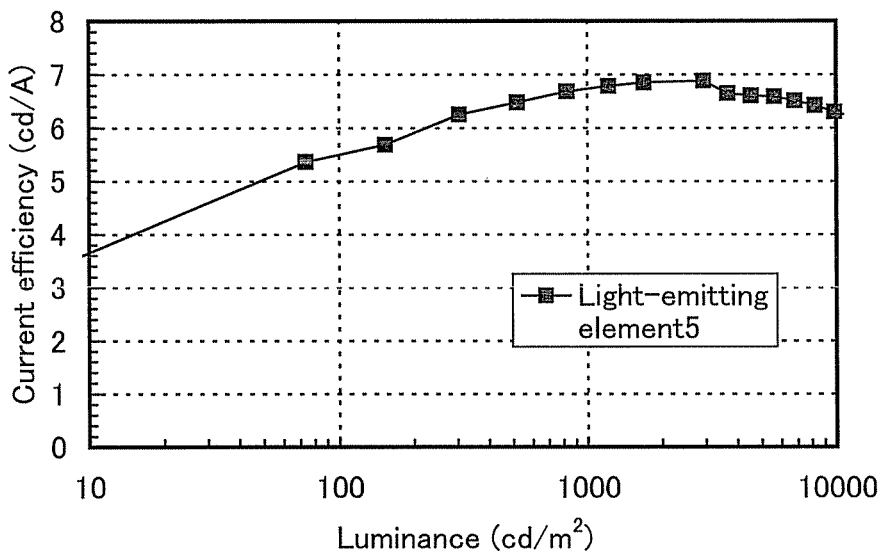
FIG. 27 shows current efficiency versus luminance characteristics of the light-emitting element 5.
Figure 28:
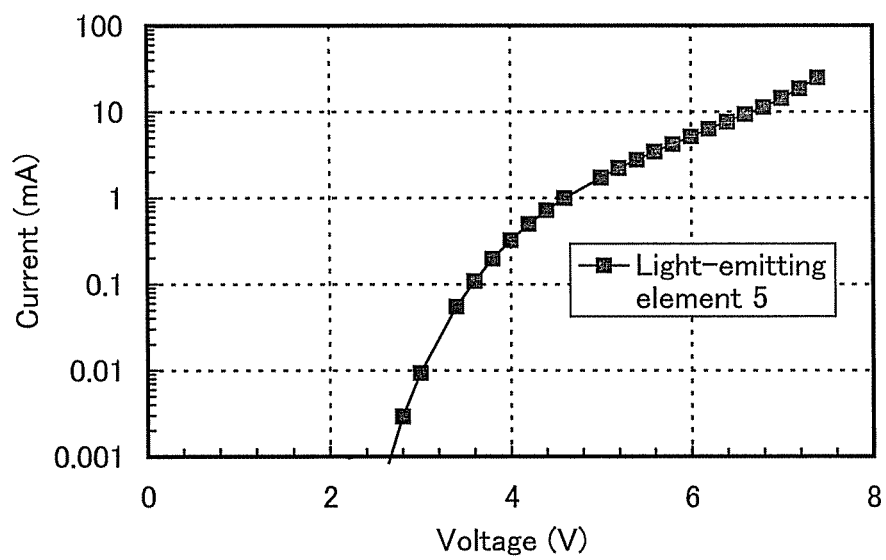
FIG. 28 shows current versus voltage characteristics of the light-emitting element 5.

FIG. 26 and FIG. 27 show that the light-emitting element 5 in which a triarylamine compound of one embodiment of the present invention was used for the light-emitting layer has low power consumption and high efficiency. FIG. 28 shows that the drive voltage of the light-emitting element is low.

Table 6 below shows initial values of main characteristics of the light-emitting element 5 at a luminance of about 1000 cd/m².

TABLE 6

| | Voltage (V) | Current (mA) | Current density (mA/cm²) | Chromaticity coordinates (x, y) | Luminance (cd/m²) | Current efficiency (cd/A) | Power efficiency (lm/W) |
|---|---|---|---|---|---|---|---|
| Light-emitting element 5 | 4.2 | 0.5 | 12 | (0.15, 0.21) | 830 | 6.7 | 5.0 |

The above results in Table 6 also show that the light-emitting element 5 manufactured in this example has high luminance and high current efficiency.

Figure 29:
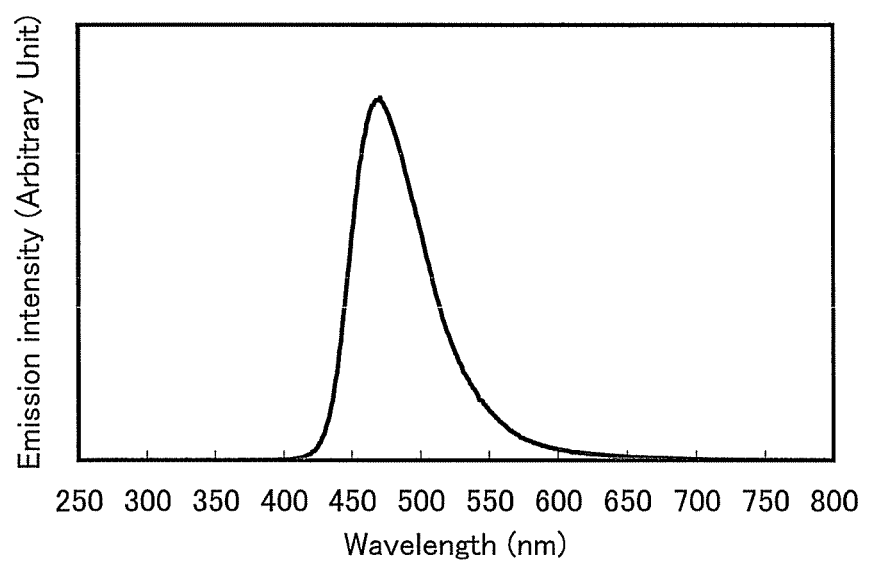
FIG. 29 shows an emission spectrum of the light-emitting element 5.
Figure 30:
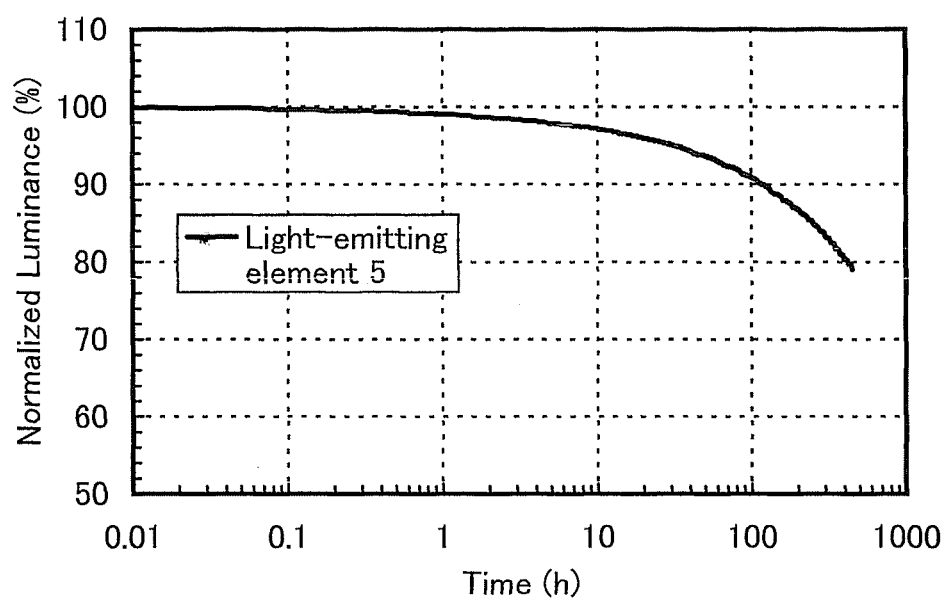
FIG. 30 shows reliability of the light-emitting element 5.

FIG. 29 shows an emission spectrum when a current at a current density of 25 mA/cm² was supplied to the light-emitting element 5. FIG. 29 shows that the emission spectrum of the light-emitting element 5 has a peak at around 473 nm, which indicates that the emission spectrum is derived from emission of BOxABP included in the light-emitting layer 1113.

Thus, BOxABP has a higher S1 level than a substance which emits blue light, and can be used for a host material or a carrier-transport material in a light-emitting element which exhibits fluorescence having a wavelength longer than or equal to that of blue light.

The light-emitting element 5 was subjected to a reliability test. Note that in the reliability test, the light-emitting element 5 was driven under the conditions where the initial luminance was set to 1000 cd/m² and the current density was constant. The light-emitting element 5 kept about 79% of the initial luminance after 450 hours elapsed. Thus, the reliability test revealed high reliability of the light-emitting element 5. In addition, it was confirmed that, by using a triarylamine compound of one embodiment of the present invention for a hole-injection layer, the light-emitting element can have a long lifetime.

This application is based on Japanese Patent Application serial no. 2011-140508 filed with the Japan Patent Office on Jun. 24, 2011, the entire contents of which are hereby incorporated by reference.

What is claimed is:

1. A compound represented by a general formula (G1),

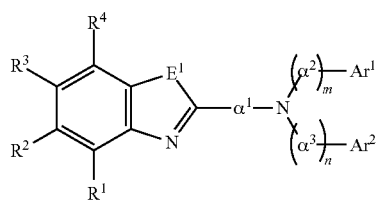
(G1)

wherein:
$E^1$ represents an oxygen atom;
$\alpha^1$ to $\alpha^3$ each independently represent a substituted or unsubstituted phenylene group or a substituted or unsubstituted biphenylene group, and m and n are each independently 0 or 1;
$Ar^1$ represents an aryl group represented by a general formula (G1-2) below;
$Ar^2$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group; and
$R^1$ to $R^4$ each independently represent any of a hydrogen atom, an alkyl group having 1 to 6 carbon atoms, and a substituted or unsubstituted phenyl group, and

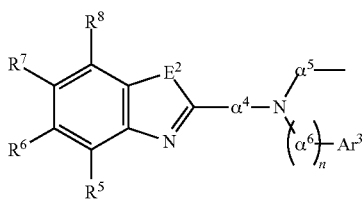
(G1-2)

wherein:
$E^2$ represents an oxygen atom;
$\alpha^4$ to $\alpha^6$ each independently represent a substituted or unsubstituted phenyl group or a substituted or unsubstituted biphenyl group, and q is 0 or 1;
$Ar^3$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group; and
$R^5$ to $R^8$ each independently represent any of a hydrogen atom, an alkyl group having 1 to 6 carbon atoms, and a substituted or unsubstituted phenyl group.

2. A light-emitting element comprising the compound according to claim 1.

3. A light-emitting device comprising the light-emitting element according to claim 2.

4. An electronic device comprising the light-emitting device according to claim 3.

5. A lighting device comprising the light-emitting device according to claim 3.

6. A compound represented by a formula (G2),

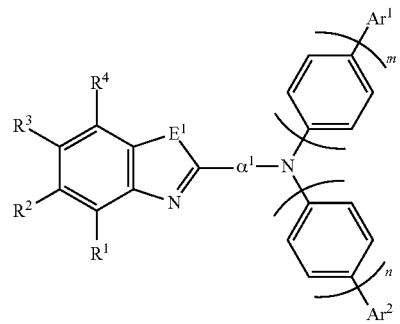
(G2)

wherein:
$E^1$ represents an oxygen atom;
$\alpha^1$ represents a substituted or unsubstituted phenylene group or a substituted or unsubstituted biphenylene group, and m and n are each independently 0 or 1;
$Ar^1$ represents an aryl group represented by a general formula (G2-2) below;
$Ar^2$ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group; and
$R^1$ to $R^4$ each independently represent any of a hydrogen atom, an alkyl group having 1 to 6 carbon atoms, and a substituted or unsubstituted phenyl group, and

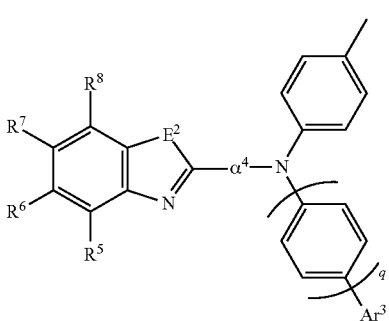
(G2-2)

wherein:
$E^2$ represents an oxygen atom;
$\alpha^4$ represents a substituted or unsubstituted phenylene group or a substituted or unsubstituted biphenylene group, and q is 0 or 1;

Ar³ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group; and R⁵ to R⁸ each independently represent any of a hydrogen atom, an alkyl group having 1 to 6 carbon atoms, and a substituted or unsubstituted phenyl group.

7. A light-emitting element comprising the compound according to claim 6.

8. A light-emitting device comprising the light-emitting element according to claim 7.

9. An electronic device comprising the light-emitting device according to claim 8.

10. A lighting device comprising the light-emitting device according to claim 8.

11. A compound represented by a formula (G3),

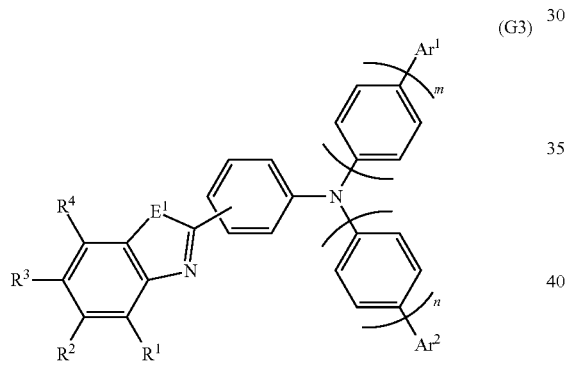

(G3)

wherein:

E¹ represents an oxygen atom;

m and n are each independently 0 or 1;

Ar¹ represents an aryl group represented by a formula (G3-2) below;

Ar² represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group; and R¹ to R⁴ each independently represent any of a hydrogen atom, an alkyl group having 1 to 6 carbon atoms, and a substituted or unsubstituted phenyl group, and

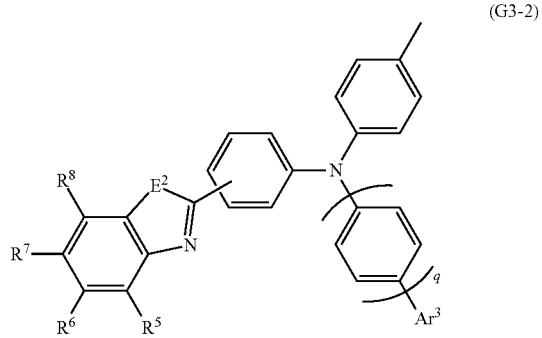

(G3-2)

wherein:

E² represents an oxygen atom;

q is 0 or 1;

Ar³ represents any of a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted carbazolyl group, a substituted or unsubstituted dibenzothiophenyl group, and a substituted or unsubstituted dibenzofuranyl group; and R⁵ to R⁸ each independently represent any of a hydrogen atom, an alkyl group having 1 to 6 carbon atoms, and a substituted or unsubstituted phenyl group.

12. A light-emitting element comprising the compound according to claim 11.

13. A light-emitting device comprising the light-emitting element according to claim 12.

14. An electronic device comprising the light-emitting device according to claim 13.

15. A lighting device comprising the light-emitting device according to claim 13.

16. A compound represented by a formula (100):

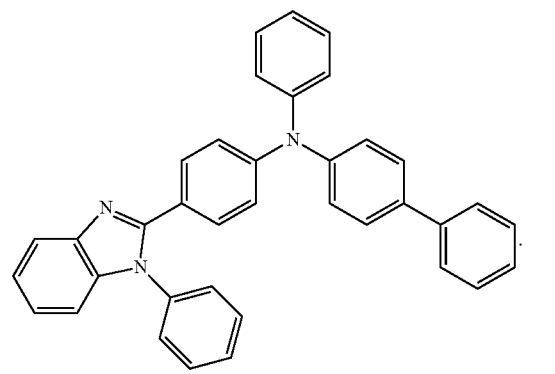

(100)

17. A light-emitting element comprising the compound according to claim 16.

18. A light-emitting device comprising the light-emitting element according to claim 17.

19. An electronic device comprising the light-emitting device according to claim 18.

20. A lighting device comprising the light-emitting device according to claim 18.

21. A compound represented by a formula (135):
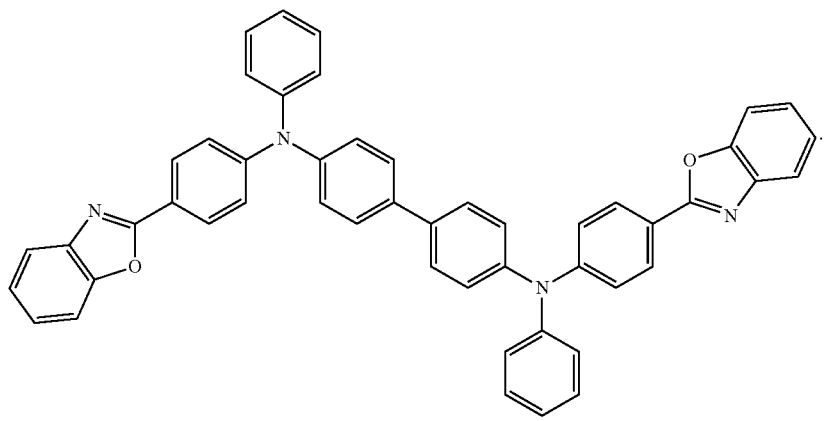
(135)
22. A light-emitting element comprising the compound according to claim 21.
23. A light-emitting device comprising the light-emitting element according to claim 22.
24. An electronic device comprising the light-emitting device according to claim 23.
25. A lighting device comprising the light-emitting device according to claim 23.
* * * * *